US009816066B2

(12) United States Patent
Geihe et al.

(10) Patent No.: US 9,816,066 B2
(45) Date of Patent: Nov. 14, 2017

(54) METHOD FOR DELIVERY OF SMALL MOLECULES AND PROTEINS ACROSS THE CELL WALL OF ALGAE USING MOLECULAR TRANSPORTERS

(71) Applicants: THE BOARD OF TRUSTEES OF THE LELAND STANFORD JUNIOR UNIVERSITY, Palo Alto, CA (US); THE REGENTS OF THE UNIVERSITY OF CALIFORNIA, Oakland, CA (US)

(72) Inventors: Erika Geihe, San Franciso, CA (US); Brian Trantow, Menlo Park, CA (US); Paul Wender, Menlo Park, CA (US); Joel M. Hyman, San Mateo, CA (US); Bahram Parvin, Mill Valley, CA (US)

(73) Assignees: The Regents of the University of California, Oakland, CA (US); The Board of Trustees of the Leland Stanford Junior University, Palo Alto, CA (US)

( * ) Notice: Subject to any disclaimer, the term of this patent is extended or adjusted under 35 U.S.C. 154(b) by 76 days.

(21) Appl. No.: 14/396,274

(22) PCT Filed: Mar. 12, 2013

(86) PCT No.: PCT/US2013/030489
§ 371 (c)(1),
(2) Date: Oct. 22, 2014

(87) PCT Pub. No.: WO2013/162729
PCT Pub. Date: Oct. 31, 2013

(65) Prior Publication Data
US 2015/0118704 A1    Apr. 30, 2015

Related U.S. Application Data

(60) Provisional application No. 61/637,481, filed on Apr. 24, 2012.

(51) Int. Cl.
| | |
|---|---|
| *C12N 1/12* | (2006.01) |
| *A61K 36/02* | (2006.01) |
| *A61K 36/05* | (2006.01) |
| *C12Q 1/24* | (2006.01) |
| *C12N 15/87* | (2006.01) |

(52) U.S. Cl.
CPC ............. *C12N 1/12* (2013.01); *C12N 15/87* (2013.01); *C12Q 1/24* (2013.01); *A61K 36/02* (2013.01); *A61K 36/05* (2013.01); *C07K 2319/10* (2013.01); *G01N 2333/405* (2013.01)

(58) Field of Classification Search
None
See application file for complete search history.

(56) References Cited

U.S. PATENT DOCUMENTS

| | | |
|---|---|---|
| 4,758,550 A | 7/1988 | Cardinaux et al. |
| 5,122,368 A | 6/1992 | Greenfield et al. |
| 6,306,993 B1 | 10/2001 | Rothbard et al. |
| 6,495,663 B1 | 12/2002 | Rothbard et al. |
| 6,593,292 B1 | 7/2003 | Rothbard et al. |
| 6,624,189 B2 | 9/2003 | Wender |
| 6,669,951 B2 | 12/2003 | Rothbard |
| 6,730,293 B1 | 5/2004 | Rothbard |
| 6,759,387 B2 | 7/2004 | Rothbard |
| 7,056,942 B2 | 6/2006 | Hildesheim et al. |
| 7,169,814 B2 | 1/2007 | Rothbard |
| 7,229,961 B2 | 6/2007 | Rothbard |

(Continued)

FOREIGN PATENT DOCUMENTS

| | | |
|---|---|---|
| WO | 9405282 | 3/1994 |
| WO | 03070719 | 8/2003 |

(Continued)

OTHER PUBLICATIONS

Sander, K and Murthy, G.S., "Enzymatic Degradation of Microalgal Cell Walls", 2009 Am. Soc. Ag. and Biol. Eng. (ASABE) Annual Intl. Mtg. (Reno, NV,Jun. 21-24, 2009) , Paper No. 1035636,12 pages.*

Wender, Paul A. et al., "The design of guanidinium-rich transporters and the ir internalization mechanisms", Advanced Drug Delivery Reviews, Mar. 1, 2008, vol. 60, pp. 452-472.

Wender, Paul A. et al., "The design, synthesis , and evaluation of molecules that enable or enhance cellular uptake: peptoid molecular transporters", PNAS, Nov. 21, 2000, vol. 97, No. 24, pp. 13003-13008, ISSN 0027-8424.

(Continued)

*Primary Examiner* — Chris R Tate
*Assistant Examiner* — Aaron J Kosar
(74) *Attorney, Agent, or Firm* — Thomas|Horstemeyer, LLP

(57) ABSTRACT

The introduction of tools to study, control or expand the inner-workings of algae has been slow to develop. Provided are embodiments of a molecular method based on guanidinium-rich molecular transporters (GR-MoTrs) for bringing molecular cargos into algal cells. The methods of the disclosure have been shown to work in wild-type algae that have an intact cell wall. Developed using *Chlamydomonas reinhardtii*, this method is also successful with less studied algae, including *Neochloris oleoabundans* and *Scenedesmus dimorphus*, thus providing a new and versatile tool for algal research and modification. The method of delivering a cargo compound to an algal cell comprises contacting an algal cell with a guanidinium-rich delivery vehicle comprising a guanidinium-rich molecular transporter (GR-MoTr) linked to a cargo compound desired to be delivered to the algal cell, whereby the guanidinium-rich molecular transporter can traverse the algal cell wall, thereby delivering the cargo compound to the algal cell.

13 Claims, 17 Drawing Sheets

(56) References Cited

U.S. PATENT DOCUMENTS

| | | | |
|---|---|---|---|
| 7,232,842 | B2 | 6/2007 | Wender |
| 7,256,286 | B2 | 8/2007 | Wender |
| 7,585,834 | B2 | 9/2009 | Wender et al. |
| 8,067,632 | B2 | 11/2011 | Wender |
| 8,278,264 | B2 | 10/2012 | Rothbard |
| 8,497,385 | B2 | 7/2013 | Wender et al. |
| 8,653,238 | B2 | 2/2014 | Wender et al. |
| 2002/0009491 | A1 | 1/2002 | Rothbard |
| 2002/0131965 | A1 | 9/2002 | Rothbard |
| 2003/0162719 | A1 | 8/2003 | Rothbard |
| 2004/0186045 | A1 | 9/2004 | Rothbard |
| 2006/0111274 | A1 | 5/2006 | Rothbard |
| 2007/0078094 | A1 | 4/2007 | Zhao et al. |
| 2007/0173436 | A1 | 7/2007 | Rothbard |
| 2010/0081618 | A1 | 4/2010 | Wender |
| 2010/0255499 | A1 | 10/2010 | Wender |
| 2010/0280219 | A1 | 11/2010 | Cooley et al. |
| 2011/0160146 | A1 | 6/2011 | Wender |
| 2011/0206610 | A1 | 8/2011 | Rothbard |
| 2012/0225826 | A1 | 9/2012 | Wender |
| 2013/0096069 | A1 | 4/2013 | Rothbard |

FOREIGN PATENT DOCUMENTS

| | | |
|---|---|---|
| WO | 2004069159 | 8/2004 |
| WO | 2006012527 | 2/2006 |
| WO | 2008069824 | 6/2008 |
| WO | 2009099636 | 8/2009 |

OTHER PUBLICATIONS

Hyman, Joel M. et al., "A molecular method for the delivery of small molecules and proteins across the cell wall of algae using molecular transporters", PNAS, Aug. 14, 2012, vol. 109, No. 33, pp. 13225-13230. ISSN 0027-8424.
Abo-Shady et al., Chemical composition of the cell wall in some green algae species (1993) Biologia Plantarum 35: 629-632.
Azencott et al., Influence of the Cell Wall on Intracellular Delivery to Algal Cells by Electroporation and Sonication (2007) Ultrasound in Med. & Biol. 33: 1805-1817.
Casadevalli et al., Studies on Batch and Continuous Cultures of Botryococcus braunii: Hydrocarbon Production in Relation to Physiological State, Cell Ultrastructure, and Phosphate Nutrition(1985) Biotechnol. Bioeng. 27: 286-295.
Cepák et al., Comparative Study of Zooid and Non-Zooid Forming Strains of Scenedesmus obliquus. Physiology and Cytomorphology(2006) Folia Microbiol. 51: 349-356.
Chang et al., Cellular Internalization of Fluorescent Proteins via Arginine-rich Intracellular Delivery Peptide in Plant Cells(2005) Plant Cell Physiol. 46: 482-488.
Christenson & Sims Production and harvesting of microalgae for wastewater treatment, biofuels, and bioproducts (2011) Biotechnol. Adv. 29: 686-702.
Chugh & Eudes Cell-penetrating peptides From mammalian to plant cells(2007) J. Pept. Sci. 14: 477-481.
Chugh et al., Translocation of cell-penetrating peptides and delivery of their cargoes in triticale microspores(2009) Plant Cell Rep. 28: 801-810.
Constantini et al., Peptide Motifs for Insertion of Radiolabeled Biomolecules into Cells and Routing to the Nucleus for Cancer Imaging or Radiotherapeutic Applications (2008) Cancer Biotherapy and Radiopharmaceuticals 23: 3-24.
Davis et al., A review of the biochemistry of heavy metal biosorption by brown algae (2003) 37: 4311-4330.
Deshayes et al., Structural polymorphism of non-covalent peptide-based delivery systems: Highway to cellular uptake (2010) Biochim. Biophys. Acta 1798: 2304-2314.
Eggenberger et al., Passage of Trojan Peptides into Plant Cells (2009) Chembiochem 10: 2504-2512.
Zhou et al. Generation of Mouse and Human Induced Pluripotent Stem Cells (iPSC) from Primary Somatic Cells (2009) Cell Stem Cell 4: 381-384.

Hartzell et al., Mechanisms of Flagellar Excision (1993) Exp. Cell Res. 208: 148-153.
Kilian et al., High-efficiency homologous recombination in the oil-producing alga Nannochloropsis sp.(2011) 108: 21265-21269.
Kreimer G The green algal eyespot apparatus: a primordial visual system and more? (2009) Curr. Genet. 55: 19-43.
Won et al., Reducible Poly(oligo-d-arginine) for Enhanced Gene Expression in Mouse Lung by Intratracheal Injection (2010) Mol. Ther. 18: 734-742.
Liu et al., Cell Membrane Diversity in Noncovalent Protein Transduction (2008) J. Membrane. Biol. 222: 1-15.
Marshall WF Quantitative High-Throughput Assays for Flagella-Based Motility in Chlamydomonas Using Plate-Well Image Analysis and Transmission Correlation Spectroscopy(2009) J. Biomol. Screening 14: 133-141.
Mayfield et al., Chlamydomonas reinhardtii chloroplasts as protein factories (2007) Curr. Opin. Biotechnol. 18: 126-133.
Merchant et al. The Chlamydomonas Genome Reveals the Evolution of Key Animal and Plant Functions(2007) Science 318: 245-250.
Nagle & Zhou Marine Natural Products as Inhibitors of Hypoxic Signaling in Tumors (2009) Phytochem. Rev. 8: 415-429.
Park et al., Wastewater treatment high rate algal ponds for biofuel production(2011) Bioresour. Technol. 102: 35-42.
Radakovits et al., Genetic Engineering of Algae for Enhanced Biofuel Production (2010) Eukaryotic Cell 9: 486-501.
Schwarze et al., In Vivo Protein Transduction: Delivery of a Biologically Active Protein into the Mouse(1999) Science 285: 1569-1572.
Siprashvili et al. Gene Transfer via Reversible Plasmid Condensation with Cysteine-Flanked, Internally Spaced Arginine-Rich Peptides(2003) Hum. Gene Ther. 14: 1225-1233, 34-36.
Specht et al., Micro-algae come of age as a platform for recombinant protein production(2010) Biotechnol. Letters 32: 1373-1383.
Stewart et al., Cell-penetrating peptides as delivery vehicles for biology and medicine (2008) Org. Biomol. Chem. 6: 2242-2255.
Torchilin VP Tat peptide-mediated intracellular delivery of pharmaceutical nanocarriers (2008) Adv. Drug Deliv. Rev. 60: 548-558.
Tung & Weissleder Arginine containing peptides as delivery vectors (2003) Adv. Drug Delivery Reviews 55: 281-294.
Unnamalai et al., Cationic oligopeptide-mediated delivery of dsRNA for post-transcriptional gene silencing in plant cells (2004) FEBS Letters 566: 307-310.
Kirschberg et al. "Arginine-Based Molecular Transporters: The Synthesis and Chemical Evaluation of Releasable Taxol-Transporter Conjugates," Org. Lett., 2003, vol. 5, issue 19, pp. 3459-3462.
Vippagunta et al. "Crystalline Solids," Advanced Drug Delivery Reviews, 2001, vol. 48, pp. 3-26.
Vrudhula et al., "Reductively activated disulfide prodrugs of paclitaxel," Bioorganic & Medicinal Chemistry Letters, 2002, vol. 12, issue 24, pp. 3591-3594.
International Search Report, dated Sep. 29, 2008 (Application PCT/US07/05375), 11 pages.
Wender et al., Beyond Cell Penetrating Peptide: Designed Molecular Transporters, Drug Discovery Today Technology, 2012, pp. 49-55, vol. 9, issue 1.
Wender et al., Taxol-oligoarginine conjugates overcome drug resistance in-vitro in human ovarian carcinoma, Gynecologic Oncology, 2012, pp. 118-123, vol. 1.
Stanzl et al., Fifteen Years of Cell-Penetrating, Guanidinium-Rich Molecular Transporters: Basic Science, Research Tools, and Clinical Applications, Accounts of Chemical Research, May 22, 2013, 11 pages.
Brooks et al. (Toxicon, 1987, 25(11), 1229-1233).
Zayed et al. (Planta Medica, 1984, 50(1), 65-69).
Kinzel et al. Stimulation of Choline Incorporation in Cell Cultures by Phorbol Derivatives and Its Correlation with Their Irritant and Tumor-promoting Activity (Cancer Research, 1979, 39, 2745-2750).
Sorg et al. (Carcinogenesis, 1988, 9, 1829-1834).
Hergenhahn et al. (J. Cancer Res. Clin. Oncol., 1984, 108, 98-109.

(56) References Cited

OTHER PUBLICATIONS

Wender, et al; The Practical Synthesis of a Novel and Highly Potent Analogue of Bryostatin; J.Am. Chem. Soc. 2002, 124, 13648-13649.

Wender, et al.; Efficient Synthetic Access to a New Family of Highly Potent Bryostatin Analogues Via a Prins-Driven Macrocyclizatio Strategy; J. Am. Chem. Soc. 2008, 130, 6658-6659.

Boto, et al.; Distinct Modulatory Effects of Bryostatin 1 and Staurosporine on the Biosynthesis and Expression of the HIV Receptor Protein (CD4) by T Cells; Cell Regulation, vol. 2, 95-103, Feb. 1991.

Esa, et al.; Activation off-Cells by Bryostatins: Induction of the IL-2 Receptor Gene Transcription and Down-Modulation of Surface Receptors; Int. J. Immunopharmac., vol. 12, No. 5, pp. 481-490, 1990.

Qatsha, et al.; Go6976, a Selective Inhibitor of Protein Kinase C, is a potent Antagonist of Human Immunodeficiency Virus 1 Induction From Latent/Low-Level-Producing Reservoir Cells in Vitro; Proc. Natl. Acad. Sci. USA; vol. 90, pp. 4674-4678, May 1993.

Wender; et al.; Modeling of the Bryostatins to the Phorbol Este Pharmacophore on Portein Kinase C; Proc. Natl Acad. Sci., USA; vol. 85,pp. 7197-7201, Oct. 1988.

Pettit, et al.; Isolation and Structure of Bryostatin 1; J. Am. Chem. Soc.; 1982, 104, 6846-6848.

Kinter, et al.; Direct and Cytokine-Mediated Activation of Protein Kinase C Induces Human Immunodeficiency Virus Expression in Chronically Infected Promonocytic Cells; Journal of Virology, Sep. 1990, p. 4306-4312.

Hale, et al.; New Approaches to the Total Synthesis of the Bryostatin Antitumor Macrolides; Chem. Asian J., 2010, 5, 704-754.

Greer et al 2002. Imaging of light emission from the expression of luciferases in living cells and organism: a review. Luminescence. 17:43-74.

Zhang et al., ABCG2/BCRP Expression Modulates D-Luciferin-Based Bioluminescence Imaging, (2007) Cancer Research, pp. 9389-9397, vol. 67.

Jones et al., Releasable Luciferin-Transporter Conjugates: Tools for the Real-Time Analysis of Cellular Uptake and Release (2006) Journal of the American Chemical Society, pp. 6526-6527, vol. 128.

Dubikovskya et al., Overcoming Multiple Resistance of Small-Molecule Therapeutics Through Conjugation with Releasable Octaarginine Transporters (2008) Proceedings of the National Academy of Science U.S.A., pp. 12128-12133, vol. 105.

Wender et al., (2006) Design, Synthesis, and Biological Evaluation of a Potent, PKC Selective, B-Ring Analog of Bryostatin. Organic Letters, 8(9):1893-1896.

\* cited by examiner

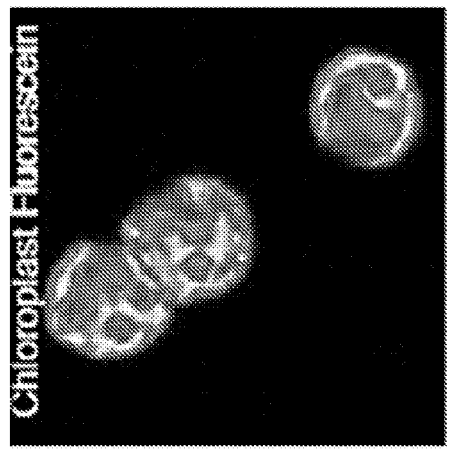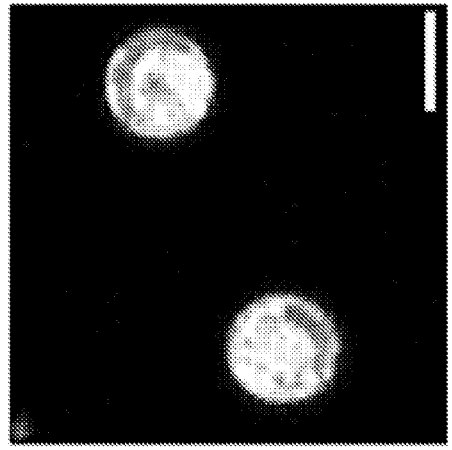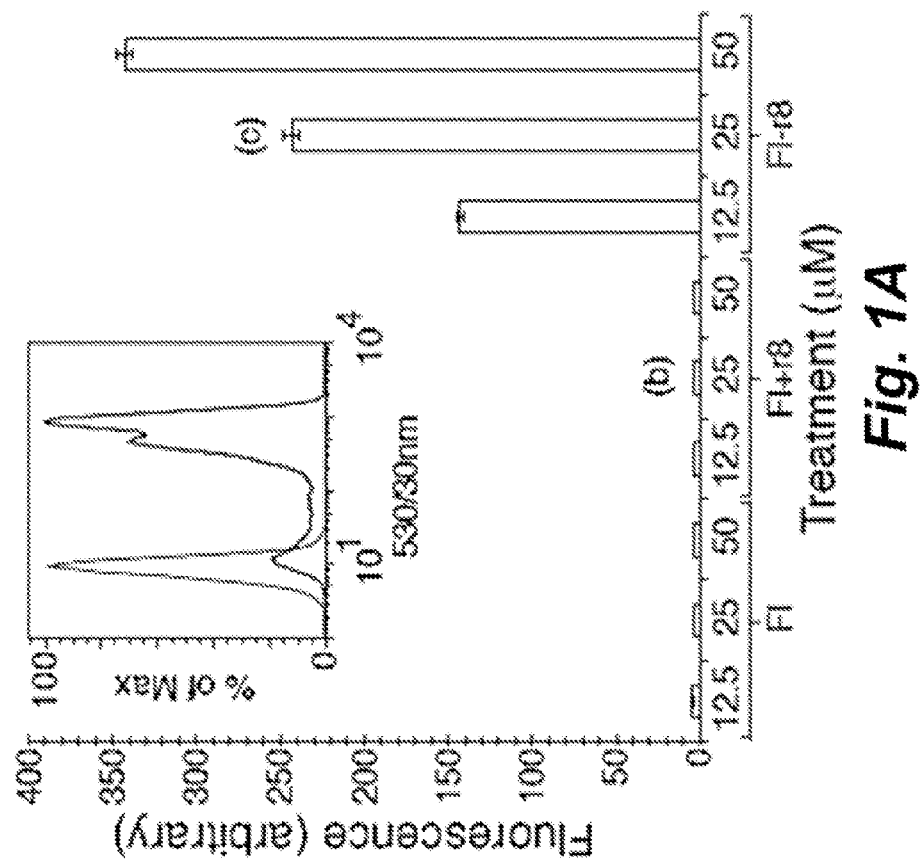

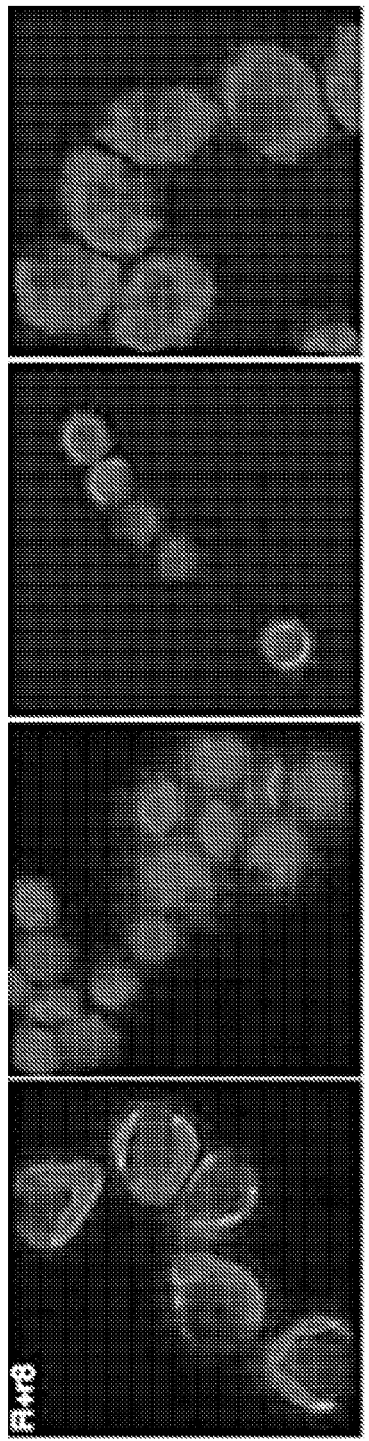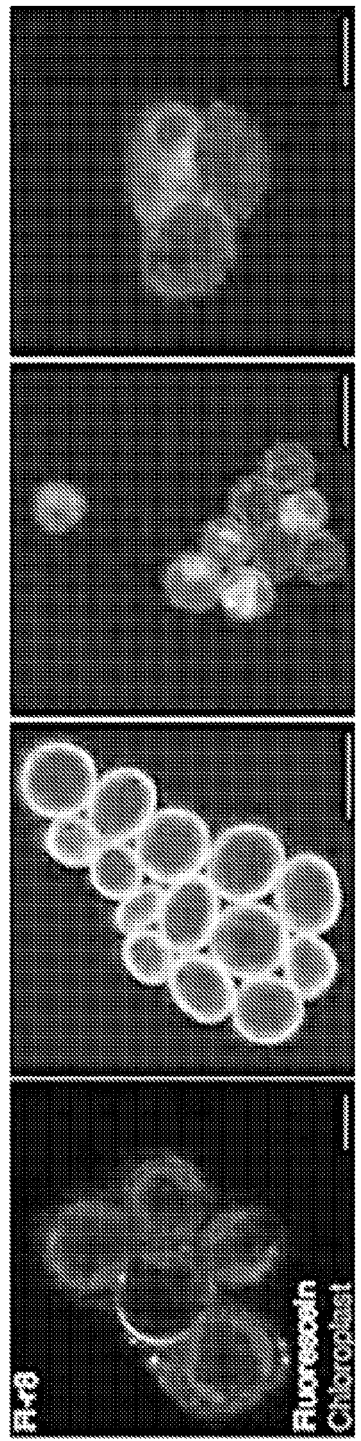

Fig. 6  n = 3, 7, 9

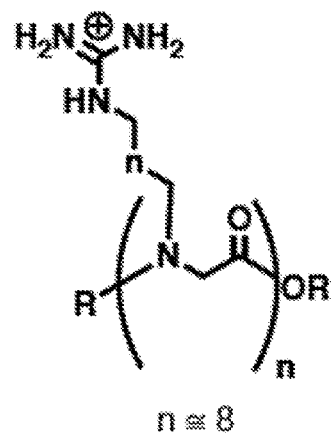
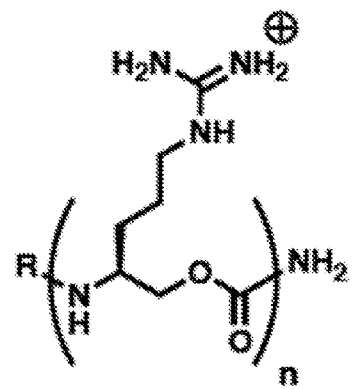
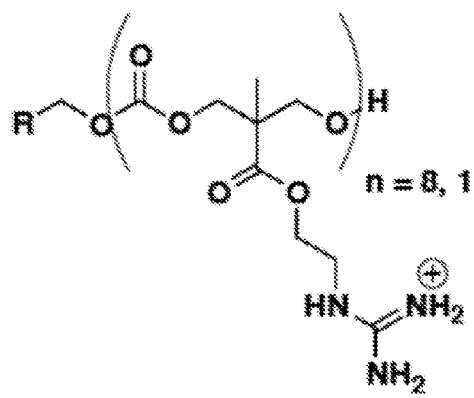
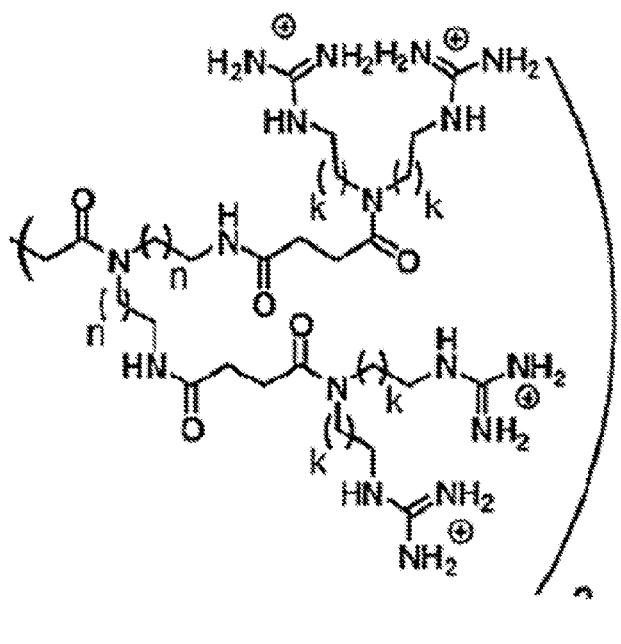
Fig. 10

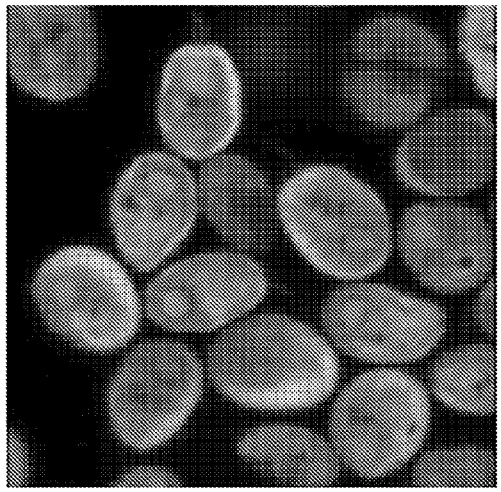
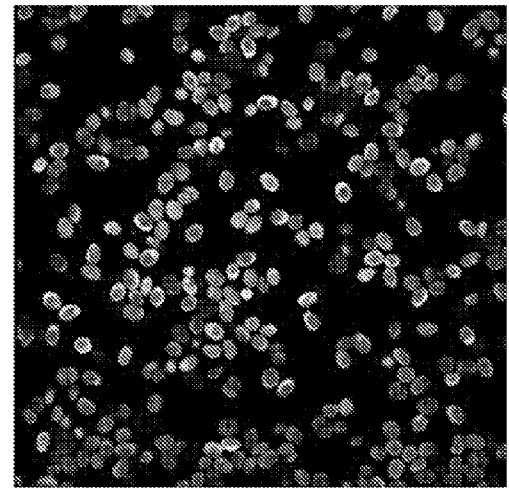
*Fig. 11A*  *Fig. 11B*
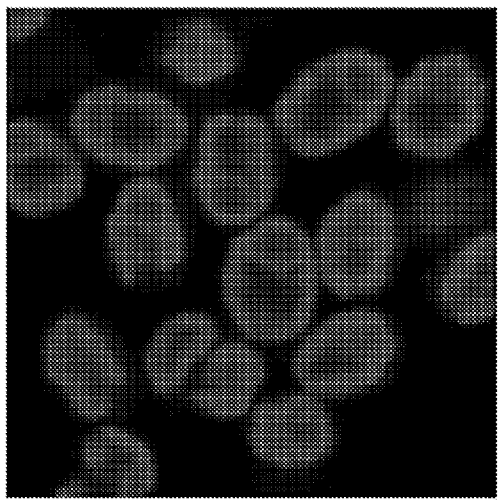
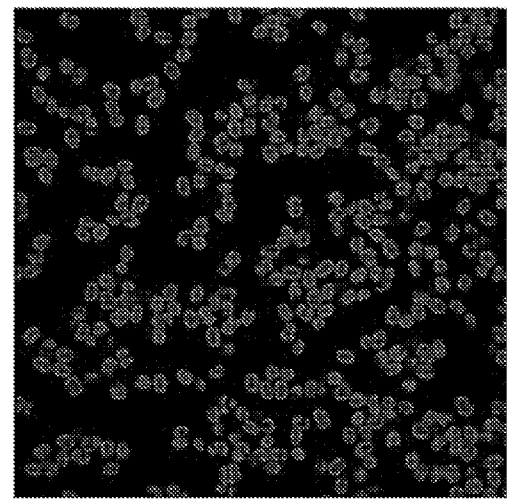
*Fig. 11C*  *Fig. 11D*

METHOD FOR DELIVERY OF SMALL MOLECULES AND PROTEINS ACROSS THE CELL WALL OF ALGAE USING MOLECULAR TRANSPORTERS

CROSS-REFERENCE TO RELATED APPLICATIONS

This application is the 35 U.S.C. §371 national stage of PCT Application No. PCT/US2013/030489, entitled "Method for Delivery of Small Molecules and Proteins Across the Cell Wall of Algae using Molecular Transporters" and filed Mar. 12, 2013, which is hereby incorporated by reference in its entirety, and which claims priority to, and the benefit of, United States Provisional Application No. 61/637,481, filed Apr. 24, 2012, which is hereby incorporated by reference in its entirety.

STATEMENT REGARDING FEDERALLY SPONSORED RESEARCH OR DEVELOPMENT

This invention was made with Government support under contract DE-AC02-05CH11231 awarded by the Department of Energy, under contract CA31841 awarded by the National Institutes of Health, and under contract CA31845 awarded by the National Institutes of Health. The Government has certain rights in this invention.

TECHNICAL FIELD

The present disclosure is generally related to the use of molecular transporters for the delivery of peptides, polypeptides, nucleic acids and small molecules across an algal cell wall and their delivery to an algal cell.

BACKGROUND

Algae represent a potentially inexpensive, scalable, $CO_2$-fixing, solar-powered source of diverse chemical products including biofuels, synthetic building blocks, nanomaterials, recombinant proteins, vaccines, antibodies, medicinal leads and food additives (Specht et al., (2010) *Biotechnol. Letters* 32: 1373-1383; Christenson &, Sims (2011) *Biotechnol. Adv.* 29: 686-702; Radakovits et al., (2010) *Eukaryotic Cell* 9: 486-501; Park et al., (2011) *Bioresour. Technol.* 102: 35-42; Mayfield et al., (2007) *Curr. Opin. Biotechnol.* 18: 126-133). They are also promising organisms for drug discovery and screening and have recognized value for bioremediation and as biosensors (Davis et al., (2003) 37: 4311-4330; Marshall WF (2009) *J. Biomol. Screening* 14: 133-141; Nagle & Zhou (2009) *Phytochem. Rev.* 8: 415-429). However, as encountered in the delivery of agents (e.g., siRNA and biologics) into mammalian cells, efforts to study or control the inner-workings of algal cells, as required for numerous research and commercial applications, are severely limited by problems encountered in the delivery of probes, genes and biomacromolecules across algal cell wall and membrane barriers. The delivery of chemical and biological agents into algal cells has been limited to physical and mechanical techniques (e.g. glass bead transfection, microinjection, electroporation, sonication, and biolistic methods) that are primarily used with cell wall-deficient mutants (Azencott et al., (2007) *Ultrasound in Med. & Biol.* 33: 1805-1817; Harris EH (2009) *The Chlamydomonas Sourcebook, Second Edition*. 1: 293-302; Kilian et al., (2011) 108: 21265-21269). While effective for many applications, these delivery methods are not scalable, show high variability within a given cell population, and can produce cellular damage and contamination (for instance, biolistic gold or tungsten particles). A molecular method to deliver, on variable scale, small molecules, probes, and biomacromolecules across the cell wall and membrane of wild-type algae, as required to probe and manipulate intracellular pathways in intact algae, would enable new opportunities in algal research and in the use of algae as photoautotrophic tools for synthetic biology. At the same time, such studies would serve to advance our understanding of biological barriers, a goal of central significance in the life sciences and agricultural and medical research.

It has been shown previously that the ability of guanidinium-rich molecular transporters (GR-MoTrs), including guanidinium-rich cell-penetrating peptides and non-peptidic agents, to enter mammalian cells is related to the number and spatial array of their guanidinium groups (Wender et al. (2000) *Proc. Natl. Acad. Sci. USA* 97: 13003-13008). Subsequent studies have shown that GR-MoTrs enable or enhance the delivery of a variety of cargos, including small molecules, metals, imaging agents, iron particles, and proteins, into a variety of mammalian cell types (Wender et al., (2008) *Adv. Drug Deliv. Rev.* 60: 452-472; Wender et al., (2011) *Drug Discovery Today: Technologies;* Tung & Weissleder (2003) *Adv. Drug Delivery Reviews* 55: 281-294; Torchilin V P (2008) *Adv. Drug Deliv. Rev.* 60: 548-558). GR-MoTr-drug conjugates have also advanced to clinical trials for various indications including stroke, psoriasis, and ischemic damage (Johnson et al., (2011) *Cell-Penetrating Peptides: Methods and Protocols,* 535-551). Despite this progress on mammalian cells, little is known about the ability of GR-MoTrs to enter non-mammalian cells, especially those organisms of research and commercial significance which possess a cell wall. Only a few studies of GR-MoTrs with plant cells have been reported (Chang et al., (2005) *Plant Cell Physiol.* 46: 482-488; Chugh & Eudes (2007) *J. Pept. Sci.* 14: 477-481; Eggenberger et al., (2009) *Chembiochem* 10: 2504-2512; Chugh et al., (2009) *Plant Cell Rep.* 28: 801-810; Unnamalai et al., (2004) *FEBS Letters* 566: 307-310) and a single investigation of GR-MoTrs with algae (Liu et al., (2008) *J. Membrane. Biol.* 222: 1-15) However, in the latter study (Liu et al., (2008) *J. Membrane. Biol.* 222: 1-15), *Chlorella vulgaris*, a species of green algae with a cellulosic cell wall, was found to be impermeable to a GFP-nona-(L)-arginine fusion protein.

SUMMARY

Interest in algae has significantly accelerated with the increasing recognition of their potentially unique role in medical, materials, energy, bioremediation, and synthetic biological research. However, the introduction of tools to study, control or expand the inner-workings of algae has lagged behind. The disclosure encompasses embodiments of a molecular method based on guanidinium-rich molecular transporters (GR-MoTrs) for bringing small and large cargos into algal cells. The methods of the disclosure have been shown to work in wild-type algae that have an intact cell wall. Developed using *Chlamydomonas reinhardtii*, this method is also successful with less studied algae, including *Neochloris oleoabundans* and *Scenedesmus dimorphus*, thus providing a new and versatile tool for algal research and modification.

One aspect of the present disclosure, therefore, encompasses embodiments of a method of delivering a cargo compound to an algal cell, comprising contacting an algal cell with a composition comprising a guanidinium-rich delivery vehicle comprising a guanidinium-rich molecular transporter (GR-MoTr) linked to a cargo compound desired to be delivered to the algal cell, whereby the guanidinium-rich molecular transporter can traverse the algal cell wall, thereby delivering the cargo compound to the algal cell.

In embodiments of this aspect of the disclosure, the guanidinium-rich molecular transporter can be a guanidinium-rich cell-penetrating peptide comprising from about 6 to about 25 guanidinium side-chains where at least three of the guanidinium side-chains are contiguous.

In embodiments of this aspect of the disclosure, the guanidinium-rich delivery vehicle can further comprise a linker moiety disposed between the guanidinium-rich molecular transporter (GR-MoTr) and the cargo compound.

In embodiments of this aspect of the disclosure, the linker can be cleavable.

In embodiments of this aspect of the disclosure, the cargo compound can be a small molecule, a nucleic acid, or a peptide.

In embodiments of this aspect of the disclosure, the small molecule can be a reporter molecule, an imaging contrast agent, an enzyme agonist, an enzyme antagonist, and a gene expression modulator.

In embodiments of this aspect of the disclosure, the algal cell is a member of an algal group selected from the group consisting of: Chlorophyceae Bacillariophyceae, Eustigmatophyceae, and Chrysophyceae.

In embodiments of this aspect of the disclosure, the algal cell is a *Chlamydomonas* species, a *Botryococcus* species, a *Chlorella* species, a *Neochloris* species, and a *Scenedesmus* species.

In embodiments of this aspect of the disclosure, the algal cell is *Chlamydomonas reinhardtii*, *Botryococcus braunii*, *Chlorella protothecoides*, *Neochloris oleoabundans*, or *Scenedesmus dimorphus*.

Another aspect of the disclosure encompasses embodiments of a method of isolating a sub-population of algal cells from a mixture of algal species, comprising: (a) contacting a population of algal cells with a composition comprising a guanidinium-rich delivery vehicle comprising a guanidinium-rich molecular transporter (GR-MoTr) linked to a label moiety, whereby the guanidinium-rich molecular transporter traverses the cell walls of a sub-population of algal cells, thereby delivering the label moiety to the cells of the sub-population of algal cells; (b) detecting the label moiety in the sub-population of algal cells; and (c) isolating the sub-population of algal cells, wherein said sub-population is characterized as having the capacity to receive a guanidinium-rich delivery vehicle across the cell walls thereof.

In embodiments of this aspect of the disclosure, the population of algal cells is a heterogeneous population of algal species.

In embodiments of this aspect of the disclosure, the label moiety is a fluorescent label and the sub-population of algal cells is isolated by FACS.

BRIEF DESCRIPTION OF THE DRAWINGS

Further aspects of the present disclosure will be more readily appreciated upon review of the detailed description of its various embodiments, described below, when taken in conjunction with the accompanying drawings.

FIGS. 1A-1F illustrate the results of flow cytometry and fluorescence microscopy of cell wall-deficient or wild-type *C. reinhardtii* treated with Fl, non-covalent Fl+r8, or Fl–8 conjugate.

FIG. 1A shows a graph of the mean fluorescence from flow cytometry of cell wall-deficient *C. reinhardtii*. Inset is a representative histogram from a single condition in the flow cytometry data, where left peak is the Fl+r8 control and the right peak is Fl–8, both at 25 μM FIG. 1B is a digital image of confocal Z-layers of cell wall-deficient cells treated with the non-covalent Fl+r8 control showing no apparent internalization. Scale bar equals 5 μm.

FIG. 1C is a digital image of confocal Z-layers of cell wall-deficient cells treated with fluorescein conjugate (Fl–8) showing internalization and not surface staining. Scale bar equals 5 μm.

FIG. 1D shows a graph of the mean fluorescence from flow cytometry of wild-type *C. reinhardtii*. Inset is a representative histogram from a single condition in the flow cytometry data, where left peak is the Fl+r8 control and the right peak is Fl–8, both at 25 μM.

FIG. 1E is a digital image of confocal Z-layers of wild-type cells treated with the non-covalent Fl+r8 control showing no apparent internalization. Scale bar equals 5 μm.

FIG. 1F is a digital image of confocal Z-layers of wild-type cells treated with fluorescein conjugate (Fl–8) showing internalization and not surface staining. Scale bar equals 5 μm.

FIG. 2A is a graph showing cell wall-deficient cc-4350 treated at room temperature vs. 4° C.

FIG. 2B is a graph showing wild-type cc-124 treated at room temperature vs. 4° C.

FIG. 2C is a graph showing treatment of wild-type cc-124 in the dark vs. ambient light.

FIG. 2D is a graph showing wild-type cc-124 cells deflagellated and one sample immediately treated while a second sample was allowed to recover for 20 min and then treated.

FIGS. 3A-3H is a series of digital images illustrating the results of fluorescence microscopy and flow cytometry of various algal species treated with Fl, non-covalent Fl+r8, or Fl–8. Cells were treated with Fl+r8 or Fl–8 at 25 μM for all fluorescence images, scale bar equals 5 μm. *Botryococcus braunii* treated with the control mixture Fl+r8 (FIG. 3A) showed no uptake and with Fl–8 conjugate (FIG. 3B) showed sporadic surface labeling. *Chlorella protothecoides* treated with Fl+r8 (FIG. 3C) showed no labeling and with Fl–8 conjugate (FIG. 3D) showed surface staining. *Neochloris oleoabundans* treated with Fl+r8 FIG. 3E showed no uptake and with Fl–8 conjugate (FIG. 3F) showed uptake. *Scenedesmus dimorphus* treated with Fl+r8 (FIG. 3G) showed no uptake and with Fl–8 conjugate (FIG. 3F) showed a heterogeneous profile within a given sample, with some cells showing uptake of Fl–8, some showing surface labeling and others having no apparent labeling.

FIGS. 4A and 4C show cells treated with a FAM-streptavidin-biotin-R9 complex showing internalization as well as cell wall binding. Scale bar equals 5 µm.

FIG. 4B shows that cells treated with the control FAM-streptavidin at the same concentration show no indication of binding or uptake. Scale bar equals 5 µm.

FIG. 4D is a graph showing the mean fluorescence from flow cytometry indicating the level of uptake for FAM-streptavidin and nona-arginine vs. FAM-streptavidin-biotin-R9 complex.

FIG. 10 illustrates general structures of peptoid, oligocarbamate, dendrimer, and oligocarbonate guanidinium-rich molecular transporters (GR-MoTr) suitable for use in the methods of the disclosure.

FIGS. 11A-11H shows a series of digital images from fluorescence microscopy of wild-type *C. reinhardtii* showing delivery of an active enzyme. Wild-type cells were treated with HRP-streptavidin:biotin-R9 complex (FIGS. 11A and 11B), HRP-streptavidin and nona-arginine mixture (FIGS. 11C and 11D), and HRP-streptavidin alone (FIGS. 11E and 11F) and incubated with a chemical detection reagent for HRP (HRP substrate) that is converted to a fluorescent product after turnover by the enzyme. Only cells treated with HRP-streptavidin:biotin-R9 complex followed by the HRP substrate show any fluorescent signal. (Panels G and H) Wild-type cells treated with HRP-streptavidin: biotin-R9 complex and not treated with the HRP substrate (FIGS. 11G and 11H) showed no fluorescence. Microscope settings were the same for all high-resolution images and all low-resolution images, respectively.

Figure 1E:
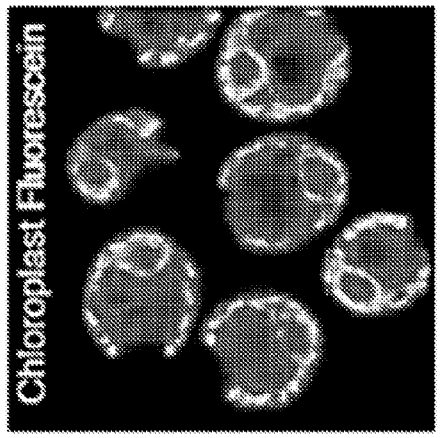

The drawings are described in greater detail in the description and examples below.

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. Patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein.

Abbreviations

Fl, fluorescein; Fl+r8, non-covalent mixture of fluorescein and r8; Fl–8, the conjugate of fluorescein and r8;

Definitions

The terms "algae" and "algal cells" as used herein refer to a large and diverse group of simple, typically autotrophic organisms, ranging from unicellular to multicellular forms. They are photosynthetic, like plants, and "simple" because they lack the many distinct organs found in land plants. All true algae have a nucleus enclosed within a membrane and chloroplasts bound in one or more membranes. "Microalgae" or "microphytes" (also referred to as phytoplankton, or planktonic algae) are microscopic algae, typically found in freshwater and marine systems. There are 200,000-800,000 species exist of which about 35,000 species are described. They are unicellular species which exist individually, or in chains or groups. Depending on the species, their sizes can range from a few micrometers (μm) to a few hundreds of micrometers. The chemical composition of microalgae is not an intrinsic constant factor but varies over a wide range, both depending on species and on cultivation conditions.

Examples of green algae include members, but are not limited to, of the *Chlamydomonas* species, including *Chlamydomonas reinhardtii*; the *Chlorella* species, the *Volvox* species, and some marine macrophytes. *C. reinhardtii*, a unicellular eukaryotic green algae is particularly advantageous for use in the methods of the present disclosure. *C. reinhardtii* grows vegetatively through mitotic division of haploid cells. Haploid cells are of either the (–) or (+) mating type. When grown in the absence of nitrogen, haploid cells of opposite mating types associate, are held together through their flagella, and eventually fuse to form a diploid zygospore. The diploid zygote undergoes meiosis and releases four haploid cells that resume the vegetative life cycle. *Chlamydomonas reinhardtii* grows rapidly and is easily and inexpensively grown in culture. Auxotrophic mutants (mutants that differ from the wild-type in requiring one or more nutritional supplements for growth) are readily available at the *Chlamydomonas* Genetic Stock Center. *C. reinhardtii* is useful for delivering antigens to animals. *C. reinhardtii* is a potential food source for animals, especially larval fish and marine invertebrates (*C. reinhardtii* is non-toxic and nonpathogenic. Both freshwater *C. reinhardtii* and a related marine species, *C. pulsatilla*, are available for administering antigens to aquatic organisms in both environments.

Although there are advantages to the use of *C. reinhardtii* as an experimental organism that may be modified for use as a food, etc., the methods of the present disclosure are contemplated to be generally useful for the delivery of small molecules, peptides, nucleic acids, and the like into the cytoplasm of a wide variety of algal species, both freshwater and marine, unicellular and multicellular, and into species of red, green, brown algae.

Saltwater algal species include, but are not limited to, marine and brackish algal species found in nature in bodies of water such as, but not limited to, seas, oceans, and estuaries. Non-limiting examples of saltwater algal species include *Nannochloropsis* sp., *Dunaliella* sp.

Freshwater algal cells are found in nature in bodies of water such as, but not limited to, lakes and ponds. Non-limiting examples of freshwater algal species include *Scendescemus* sp., *Haemotococcus* sp. Non-limiting examples of microalgae that can be used with the methods of the invention can be members of any of the following divisions: Chlorophyta, Cyanophyta (Cyanobacteria), and Heterokontophyta. In certain embodiments, the microalgae used with the methods of the disclosure are members of one of the following classes: Chlorophyceae Bacillariophyceae, Eustigmatophyceae, and Chrysophyceae. In certain embodiments, the microalgae used with the methods of the invention are members of one of the following genera: *Nannochloropsis*, *Chlorella*, *Dunaliella*, *Scenedesmus*, *Selenastrum*, *Oscillatoria*, *Phormidium*, *Spirulina*, *Amphora*, and *Ochromonas*.

Non-limiting examples of microalgae species that can be used with the methods of the present invention include: *Achnanthes orientalis, Agmenellum* spp., *Amphiprora hyaline, Amphora coffeiformis, Amphora coffeiformis* var. *linea, Amphora coffeiformis* var. *punctata, Amphora coffeiformis* var. *taylori, Amphora coffeiformis* var. *tenuis, Amphora delicatissima, Amphora delicatissima* var. *capitata, Amphora* sp., *Anabaena, Ankistrodesmus, Ankistrodesmus falcatus, Boekelovia hooglandii, Borodinella* sp., *Botryococcus braunii, Botryococcus sudeticus, Bracteococcus minor, Bracteococcus medionucleatus, Carteria, Chaetoceros gracilis, Chaetoceros muelleri, Chaetoceros muelleri* var. *subsalsum, Chaetoceros* sp., *Chlamydomas perigranulata, Chlorella anitrata, Chlorella antarctica, Chlorella aureoviridis, Chlorella Candida, Chlorella capsulate, Chlorella desiccate, Chlorella ellipsoidea, Chlorella emersonii, Chlorella fusca, Chlorella fusca* var. *vacuolate, Chlorella glucotropha, Chlorella infusionum, Chlorella infusionum* var. *actophila, Chlorella infusionum* var. *auxenophila, Chlorella kessleri, Chlorella lobophora, Chlorella luteoviridis, Chlorella luteoviridis* var. *aureoviridis, Chlorella luteoviridis* var. *lutescens, Chlorella miniata, Chlorella minutissima, Chlorella mutabilis, Chlorella nocturna, Chlorella ovalis, Chlorella parva, Chlorella photophila, Chlorella pringsheimii, Chlorella protothecoides, Chlorella protothecoides* var. *acidicola, Chlorella regularis, Chlorella regularis* var. *minima, Chlorella regularis* var. *umbricata, Chlo-*

*rella reisiglii, Chlorella saccharophila, Chlorella saccharophila* var. *ellipsoidea, Chlorella salina, Chlorella simplex, Chlorella sorokiniana, Chlorella* sp., *Chlorella sphaerica, Chlorella stigmatophora, Chlorella vanniellii, Chlorella vulgaris, Chlorella vulgaris fo. tertia, Chlorella vulgaris* var. *autotrophica, Chlorella vulgaris* var. *viridis, Chlorella vulgaris* var. *vulgaris, Chlorella vulgaris* var. *vulgaris fo. tertia, Chlorella vulgaris* var. *vulgaris fo. viridis, Chlorella xanthella, Chlorella zofingiensis, Chlorella trebouxioides, Chlorella vulgaris, Chlorococcum infusionum, Chlorococcum* sp., *Chlorogonium, Chroomonas* sp., *Chrysosphaera* sp., *Cricosphaera* sp., *Crypthecodinium cohnii, Cryptomonas* sp., *Cyclotella cryptica, Cyclotella meneghiniana, Cyclotella* sp., *Dunaliella* sp., *Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera* sp., *Ellipsoidon* sp., *Euglena* spp., *Franceia* sp., *Fragilaria crotonensis, Fragilaria* sp., *Gleocapsa* sp., *Gloeothamnion* sp., *Haematococcus pluvialis, Hymenomonas* sp., *Isochrysis aff. galbana, Isochrysis galbana, Lepocinclis, Micractinium, Micractinium, Monoraphidium minutum, Monoraphidium* sp., *Nannochloris* sp., *Nannochloropsis salina, Nannochloropsis* sp., *Navicula acceptata, Navicula biskanterae, Navicula pseudotenelloides, Navicula pelliculosa, Navicula saprophila, Navicula* sp., *Nephrochloris* sp., *Nephroselmis* sp., *Nitschia communis, Nitzschia alexandrine, Nitzschia closterium, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia* sp., *Ochromonas* sp., *Oocystis parva, Oocystis pusilla, Oocystis* sp., *Oscillatoria limnetica, Oscillatoria* sp., *Oscillatoria subbrevis, Parachlorella kessleri, Pascheria acidophila, Pavlova* sp., *Phaeodactylum tricornutum, Phagus, Phormidium, Platymonas* sp., *Pleurochrysis carterae, Pleurochrysis dentate, Pleurochrysis* sp., *Prototheca wickerhamii, Prototheca stagnora, Prototheca portoricensis, Prototheca moriformis, Prototheca zopfii, Pseudochlorella aquatica, Pyramimonas* sp., *Pyrobotrys, Rhodococcus opacus, Sarcinoid chrysophyte, Scenedesmus armatus, Schizochytrium, Spirogyra, Spirulina platensis, Stichococcus* sp., *Synechococcus* sp., *Synechocystisf, Tagetes erecta, Tagetes patula, Tetraedron, Tetraselmis* sp., *Tetraselmis suecica, Thalassiosira weissflogii*, and *Viridiella fridericiana*.

The term "transporter" as used herein refers to molecules that enable another molecule, called the cargo molecule, to pass across a biological barrier (such as a cell membrane), or which modulate or enhance the ability of the cargo molecule to pass across a biological barrier. That is, the cargo molecule, by itself, would either not cross the barrier, or would cross the barrier in sub-optimal amounts or at a suboptimal rate; conjugation of the cargo to the transporter enables or enhances the amount of the cargo (in conjugation with the transporter) that crosses the barrier, or modulates the rate at which the cargo (in conjugation with the transporter) crosses the barrier. Note that such modulation can be an increase in the amount of cargo transported by the conjugate as compared to the unconjugated cargo; or an increase in the rate at which the cargo is transported by the conjugate as compared to the unconjugated cargo.

The following patent publications describe examples of molecules which can be used as transporter molecules in the methods of the present disclosure: U.S. Pat. No. 6,306,993 (at col. 6, line 63 to col. 9, line 47); U.S. Pat. No. 6,495,663 (col. 6, line 62 to col. 10, line 59). Particularly advantageous for use in the methods of the present disclosure are transporters comprising from 6 to 25 subunits, at least 50% of which contain a guanidino or amidino side chain moiety. For example, but not intending to be limiting, U.S. Pat. No. 6,593,292 (see col. 10, line 40 to col. 14, line 64 thereof); U.S. Pat. No. 6,669,951 (col. 11, line 35 to col. 18, line 36); U.S. Pat. No. 6,730,293 (col. 10, line 1 to col. 15, line 36); U.S. Pat. No. 6,759,387 (col. 10, line 44 to col. 16, line 26) describes transporter molecules containing guanidino or amidino moieties such as arginine amino acids. The cited patents, referred to above are hereby incorporated by reference herein in their entirety. While not intended to be limiting, examples of transporter molecules suitable for use in the method of the disclosure are shown in FIG. 10 and are also described by Wender et al., (2008) *Adv. Drug Deliv. Rev.* 60: 452-472, incorporated herein by reference in its entirety.

The term "cargo molecule" as used herein refers to a variety of molecules can be used as the cargo component of the conjugate. Biologically active molecules are one group of compounds that can be used as cargo. Biologically active molecules include, but are not limited to, metal ions (which are typically delivered as metal chelates); small organic molecules, and macromolecules such as polynucleotides and polynucleotide analogs, polypeptides (peptides and proteins) and polypeptide analogs, and polysaccharides, and polysaccharide analogs. Examples of macromolecules include, but are not limited to, small interfering RNAs (siRNA or RNAi), short hairpin RNA (shRNA), ribozymes (which optionally contains one or more 2'-deoxy nucleotide subunits for enhanced stability), peptide nucleic acids (PNA}, and the like, and peptides. Polynucleotide analogs and polypeptide analogs may have modified backbones to impart one or more desirable properties, such as increased resistance to degradation or altered water solubility. The biologically active molecule preferably has a molecular weight less than about 10 kDa, more preferably less than about 1 kDa, still more preferably less than about 600 Daltons. Suitable cargo molecules are discussed in more detail herein.

Small organic molecules: A variety of small organic molecules can be attached to the transporter as cargo. Often small organic molecules will already have suitable nucleophilic moieties, some small organic molecules may have multiple nucleophilic moieties (in which case protection of certain nucleophilic moieties may be desirable in order to limit attachment of the linker to the small organic molecule at one defined site), and other small organic molecules can be readily derivatized to contain a nucleophilic moiety.

Metal ions: Metal ions can be transported as chelates. For example, metals can be chelated by diethylenetriaminepentaacetic acid, DTPA, which can then be further derivatized, e.g. by coupling of Boc-NH—CH$_2$CHrNH$_2$ to a free carboxyl using carbodiimides or uranium reagents such as HATU, HBTU and TBTU followed by removal of the Boc group. Alternatively, metals can be complexed to porphyrins or tetrapyrrole derivatives such as phthalocyanines or texaphyrins containing a free amino group, e.g., the carboxylic acid groups of mesoporphyrin IX can be derivatized with Boc-NH—CH$_2$CH$_2$—NH$_2$ as described above for DTPA for subsequent conjugation to a linker. Iron, magnesium, zinc, copper (e.g., Cu$^{67}$), nickel, cobalt (e.g., Co$^{57}$), europium, technetium (e.g., Tc$^{99m}$), europium, yttrium (e.g., Y$^{90}$), praseodymium, gadolinium, gallium (e.g., $Ga^{67}$), or indium (e.g., $In^{111}$). In various embodiments, the metal can be a divalent metal ion, such as $Ca^{2+}$, $Mn^{2+}$, $Co^{2+}$, $Ni^{2+}$, $Zn^{2+}$, $Cd^{2+}$, $Hg^{2+}$, $Srn^{2+}$, or a trivalent metal ion such as $Mn^{3+}$, $Co^{3+}$, $Ni^{3+}$, $In^{3+}$, $Nd^{3+}$, $Sm^{3+}$, $Fe^{3+}$, $Ce^{3+}$, $Eu^{3+}$, $Gd^{3+}$, $Yb^{3+}$, $Lu^{3+}$, and the like.

Macromolecules: Macromolecules can be transported as cargo by the methods of the present disclosure. Macromolecules include, but are not limited to, proteins, plasmids, and oligosaccharides, including, but not limited to, polynucleotides and polynucleotide analogs, polypeptides (peptides and proteins) and polypeptide analogs (such as peptoids), and polysaccharides and polysaccharide analogs. Examples of polynucleotides and polynucleotide analogs include DNA, cDNA, in vitro polymerized DNA, plasmid DNA, fragments of plasmid DNA, linear DNA, vectors, (PI, PAC, BAC, YAC, artificial chromosomes), recombinant DNA, chromosomal DNA, anti-sense DNA, or derivatives of these DNAs; small interfering RNAs (siRNA or RNAi), tRNA (transfer RNA), snRNA (small nuclear RNA), rRNA (ribosomal RNA), mRNA (messenger RNA), ribozymes (which optionally contains one or more 2'-deoxy nucleotide subunits for enhanced stability), and peptide nucleic acids (PNA). Polynucleotide analogs and polypeptide analogs may have modified backbones to impart one or more desirable properties, such as increased resistance to degradation or altered water solubility. Analogs may include charged and preferably uncharged backbone analogs, such as phosphonates (preferably methyl phosphonates), phosphoramidates, thiophosphates, uncharged morpholino-based polymers, 2'-0-methyl polynucleotides, and peptide nucleic acids (PNAs). PNAs are analogs of DNA in which the backbone, comprised of N-(2-aminoethyl)glycine units, is structurally analogous to the deoxyribophosphate backbone of DNA.

Reporter molecules: Another type of molecule which can be used as cargo is a reporter molecule. Reporter molecules are molecules which can be readily detected for quantitative or qualitative analysis. Examples of reporter molecules include, but are not limited to, radioactive molecules, fluorescent molecules (e.g., rhodamines, coumarins, cyanines, fluoresceins, xanthene dyes (e.g., 4-(2,7-difluoro-6-hydroxy-3-oxo-xanthen-9-yl)benzene-1,3-dicarboxylic acid, known as OREGON GREEN™, phosphorescent molecules (e.g., metalloporphyrins, eosin, erythrosin), heavy atoms (typically chelated to an organic carrier), chemiluminescent molecules, bioluminescent molecules (e.g., luciferin, which is detected in cells when converted by luciferase to light and byproduct), biotinylated molecules which can be recognized by a labeled avidin or labeled streptavidin (where the labeled avidin or streptavidin is detected), antigenic molecules which can be recognized by a labeled antibody (where the labeled antibody is detected), and metal ions such as those described above, which can be used as diagnostic agents, imaging agents, and detection agents. As with other cargo molecules, reporter molecules can be attached to the transporter molecule by such as a linker utilizing a nucleophilic moiety on the reporter molecule.

Detection of the reporter molecule can be carried out by various means known in the art, e.g., spectroscopic detection, detection of radioactivity, electrochemical detection, or enzyme assay. The detection threshold for the signal produced by the reporter molecule should be set at a reasonable level so as to distinguish signal from background noise, for example, a signal level of a magnitude 10%, 25%, 50%, or 100% above the standard deviation of the background noise, or a signal level with about a 66% probability, more preferably about a 95% probability, still more preferably about a 99% probability, of being due to signal rather than noise.

The term "linker" as used herein refers to a variety of molecules that may conjugate to the transporter unit and to a molecule desired to be delivered to an algal cell by the methods of the disclosure. It is contemplated that a linker useful in the constructs of the disclosure may be a releasable linker whereby the cargo molecule transported to the interior of an algal cell may be released from the transporter moiety. A variety of releasable linkers can be used in the methods of the present disclosure such as, but not limited to, a disulfide moiety that may be reduced and hence cleaved in the interior of the recipient algal cell. Alternatively, but not limiting, is a proteolytically cleavable linker.

Description

GR-MoTr uptake with *Chlamydomonas reinhardtii* was initially studied because molecular and genetic techniques are well established for this organism, there are a wide variety of characterized mutants, including those exhibiting altered metabolite production and photosynthesis, and the genome is fully sequenced and annotated, allowing delivery methods to be exploited to probe gene and pathway function (Harris EH (2009) *The Chlamydomonas Sourcebook, Second Edition*. 1: 293-302; Merchant et al. (2007) *Science* 318: 245-250). Several other algae from the same class, Chlorophyceae were also studied. It was shown for the first time that GR-MoTr-mediated uptake can be achieved in *C. reinhardtii* and other algal species, providing insights on differing algal barriers and a new tool for molecular manipulation or imaging of algae as required for research and commercial development.

Figure 5:
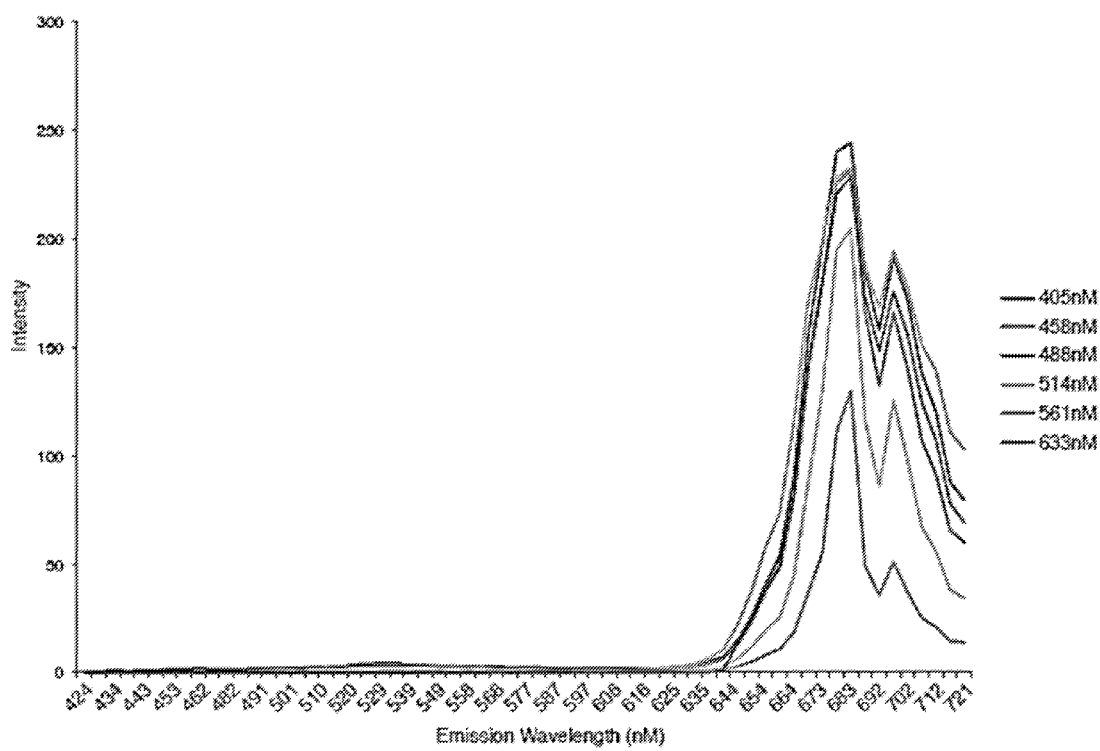
FIG. 5 illustrates the results of wavelength scans of wild-type *C. reinhardtii* at several excitation wavelengths. When illuminated with laser light at 405, 458, 488, 514, 568 or 633 nm, the *C. reinhardtii* chloroplast presents strong autofluorescence starting around 650 nm and going up past 720 nm. There is also a much weaker, yet still visible autofluorescence from approximately 450 nm to almost 600 nm. These scans indicate that bright fluorophores emitting at less than 650 nm can be used as probes without great concern about overlapping autofluorescence, while the native fluorescence from the chloroplast at about 700 nm can be used to track and image cells without the use of other dyes.
Figure 6:
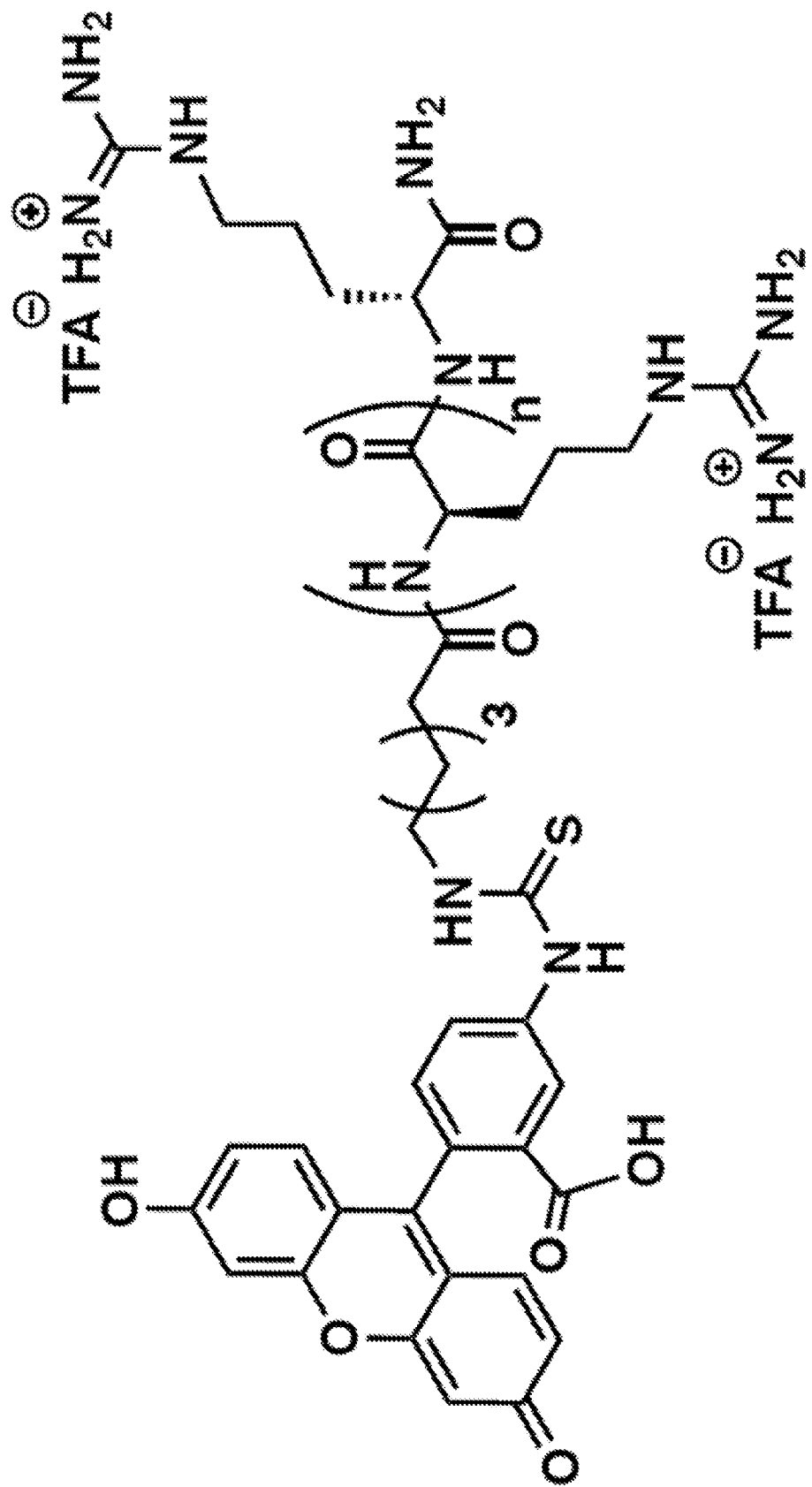
FIG. 6 illustrates the chemical structure of oligo-(D)-arginine covalently attached to fluorescein. Molecules used in this paper have n=3, 7, or 9.

Delivery of Small Molecule Probes to *Chlamydomonas reinhardtii*: To investigate GR-MoTr uptake in algae, a GR-MoTr was covalently attached to an optical probe, fluorescein. Fluorescein was selected because it does not freely enter algal cells and its fluorescence can be visualized with 488 nm laser light, thereby minimizing interference from autofluorescence. The photosynthetic machinery of green algae autofluoresces across the visible spectrum, but with lower levels of autofluorescence in the green to orange range (FIG. 5). The inherent autofluorescence of the algal chloroplast was used to track the cells by irradiating with 633 nm laser light. For this study, covalently-linked fluorescein-oligo-(D)-arginine conjugates of 4, 8, and 10 arginines (Fl–4, Fl–8, Fl–10, respectively) (FIG. 6) were synthesized following as described in Example 7 and in Wender et al. (2000) *Proc. Natl. Acad. Sci. USA* 97: 13003-13008, incorporated herein by reference in its entirety.

Access to the intracellular space and organelles of algae requires translocation across two barriers: the cell wall and cell membrane. To address passage across the latter, a *C. reinhardtii* mutant that is deficient in cell wall production (mutant cc-4350, a derivative of cw-15) was examined first. Uptake with this cell wall-deficient mutant also is more comparable to with the robust uptake of GR-MoTrs in mammalian systems (Wender et al., (2008) *Adv. Drug Deliv. Rev.* 60: 452-472).

Figure 7:
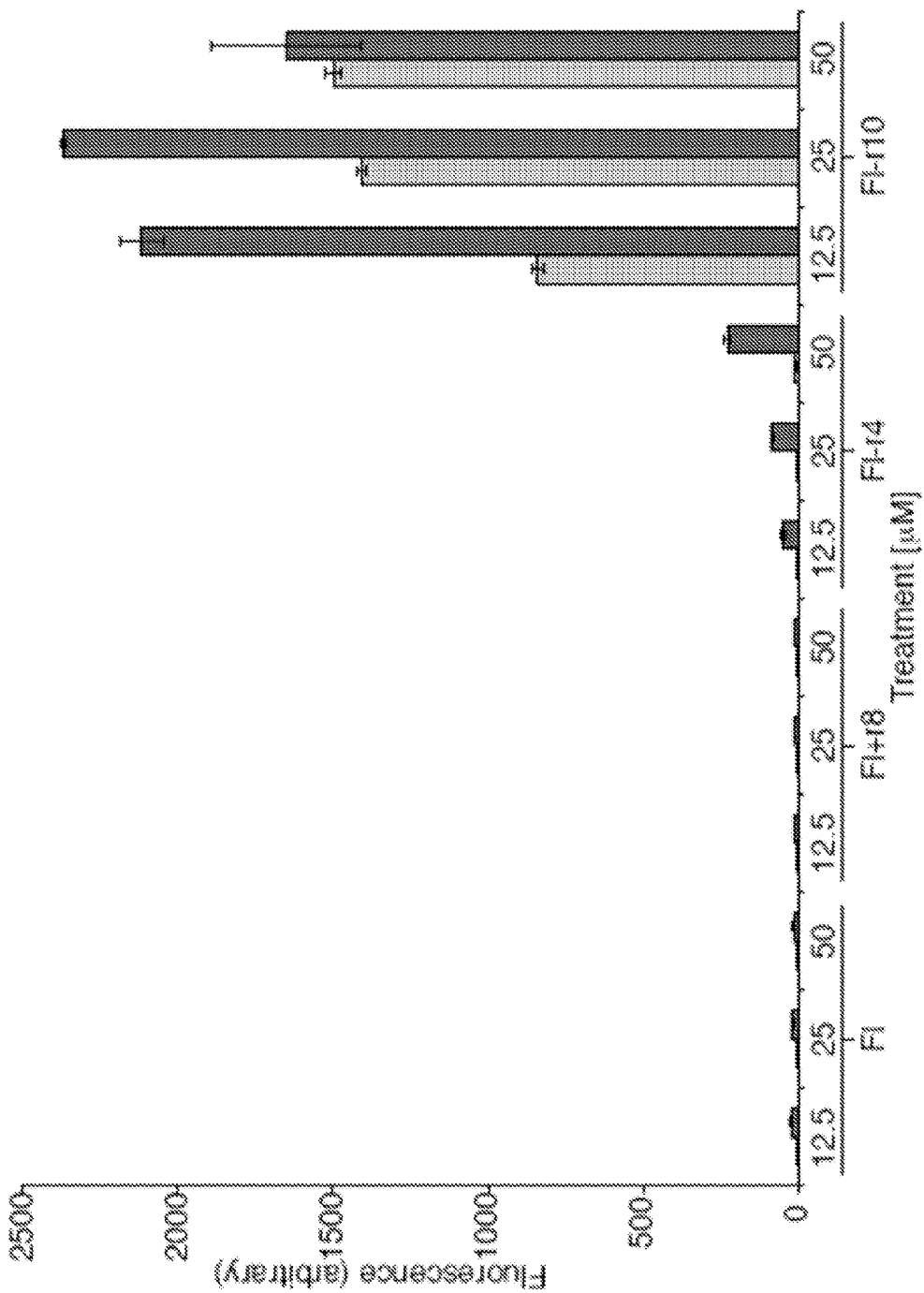
FIG. 7 is a graph illustrating the results of flow cytometry data Fl–4 and Fl–10 treatments compared to controls of Fl alone and the non-covalent mixture of Fl+r8 in cc-4350 cells and cc-124 cells. In both cases, Fl–10 treated cells show dramatic uptake.
Figure 8A:
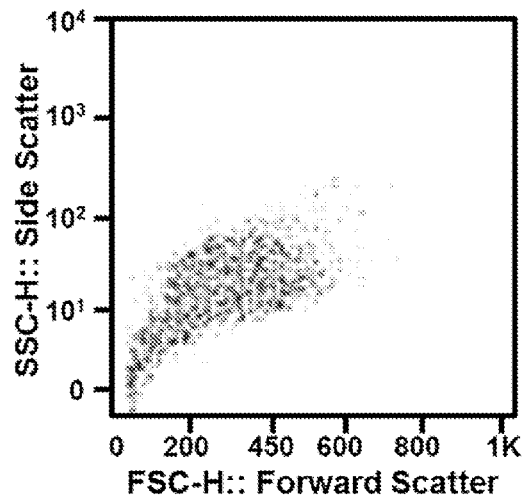
FIGS. 8A-8D is a series of images illustrating the results of the use of fluorescently labeled Gr-MoTrs along with flow cytometry to allow differentiation of species in a mixture. Flow cytometry of different algae in the family Chlorophyceae using the autofluorescence from the chloroplast does not allow differentiation of species in a mixture. The mixture is 1:1:1 of *C. reinhardtii* cc-124, *S. dimorphus*, and *N. oleoabundans*. Wild-type cells untreated (FIG. 8A) and treated (FIG. 8B) with Fl–8 and examined using forward (FSC) and side scatter (SSC) do not present any means of differentiation. Untreated cells (FIG. 8C) are still not divisible when examined using FSC and Fl–1 (530/20 nm), however, (Fl–8-treated cells FIG. 8D) are now distinctly separated and can be gated for sorting or analysis.
Figure 8B:
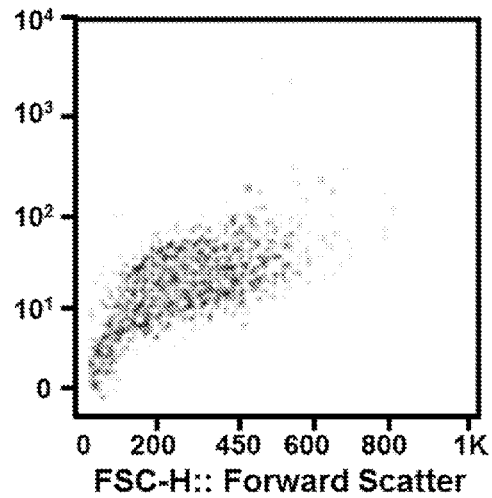
Figure 8C:
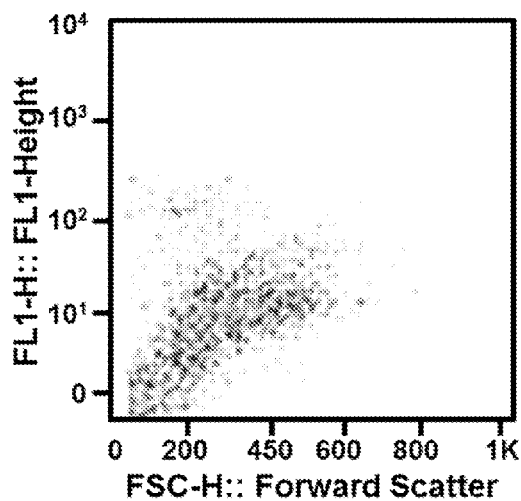
Figure 8D:
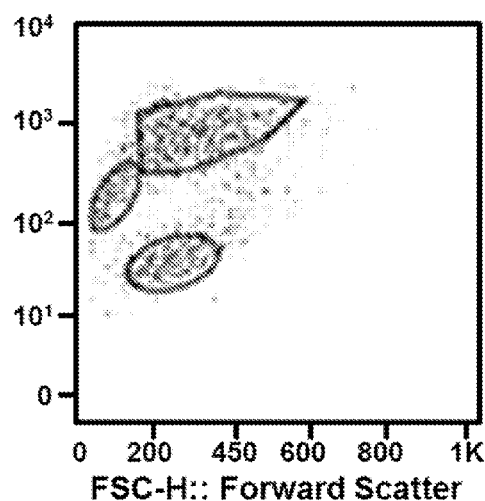
Figure 8E:
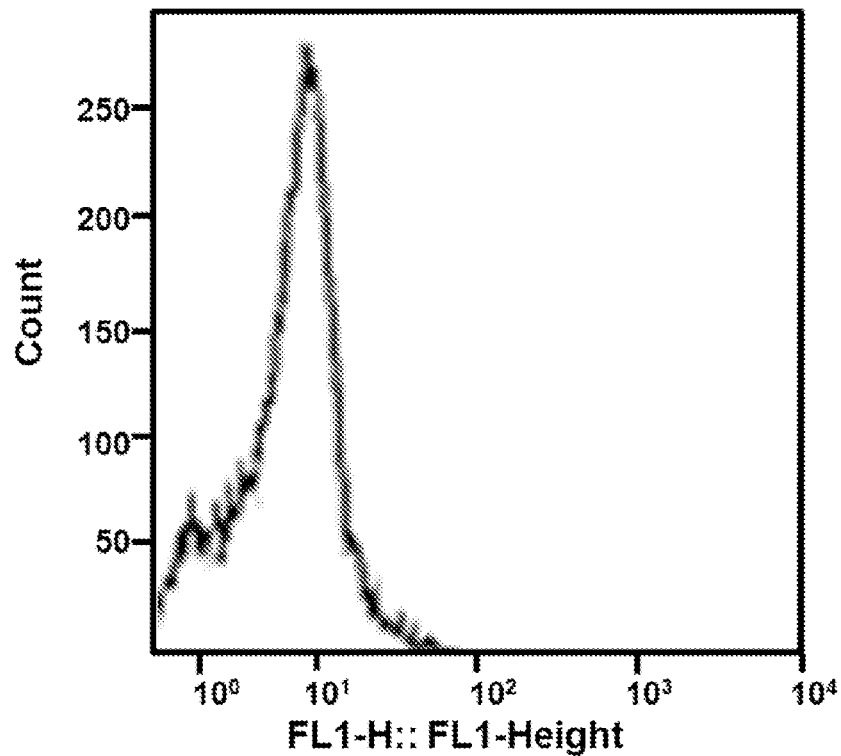
FIG. 8E and FIG. 8F are histograms showing the same results and indicating ease of separation.
Figure 8F:
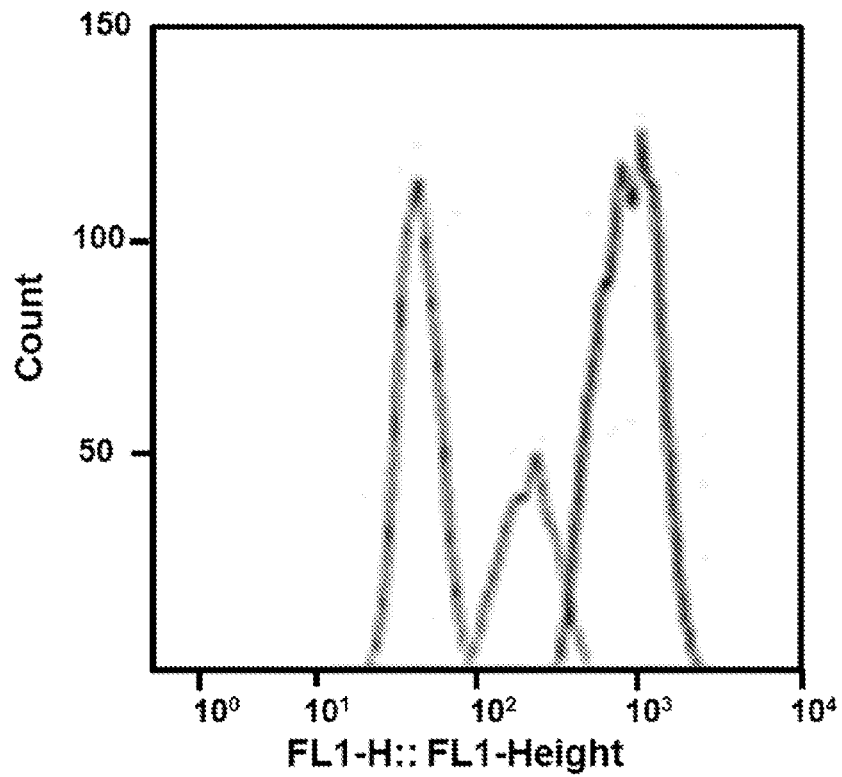
Figure 9A:
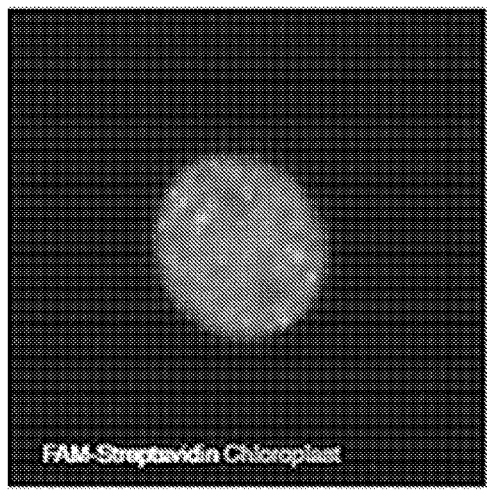
FIGS. 9A-9D illustrate the results of examples of FAM-streptavidin-biotin-R9 delivery to cells. GR-MoTrs are capable of delivering larger biomacromolecules to wild-type *C. reinhardtii* cells. Examples indicate some variability in delivery.
Figure 9B:
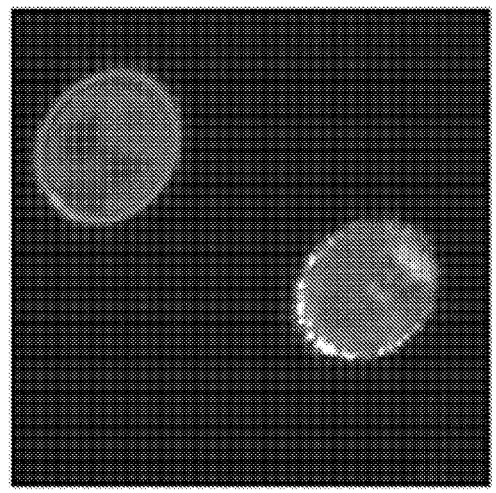
Figure 9C:
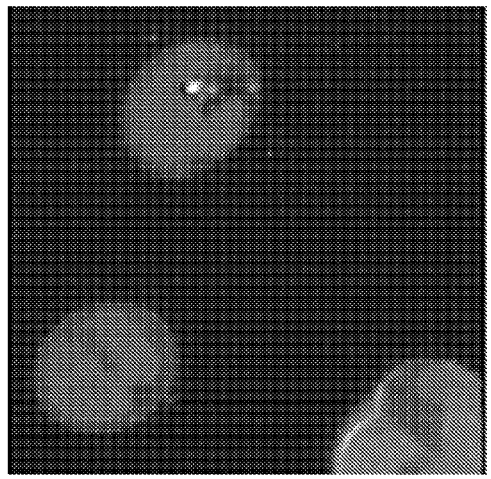
Figure 9D:
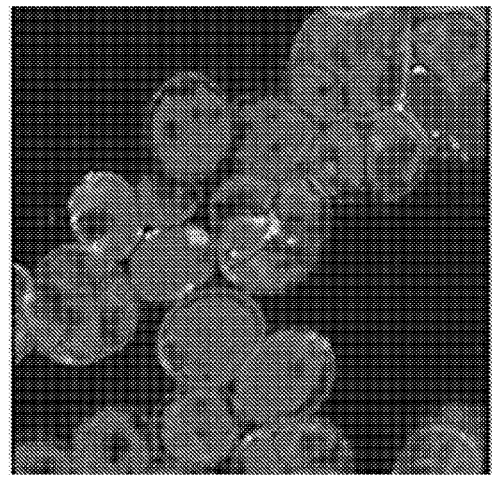
Figure 11E:
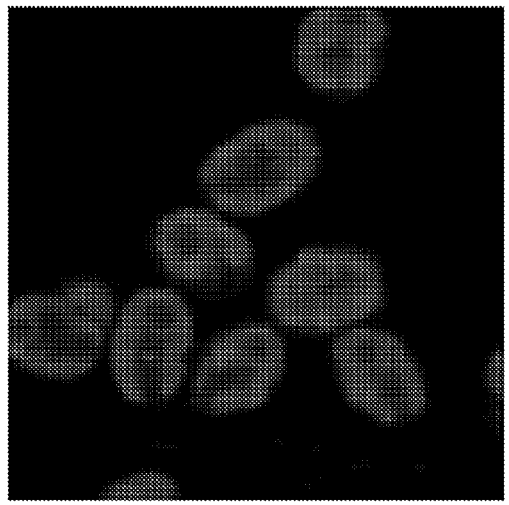
Figure 11F:
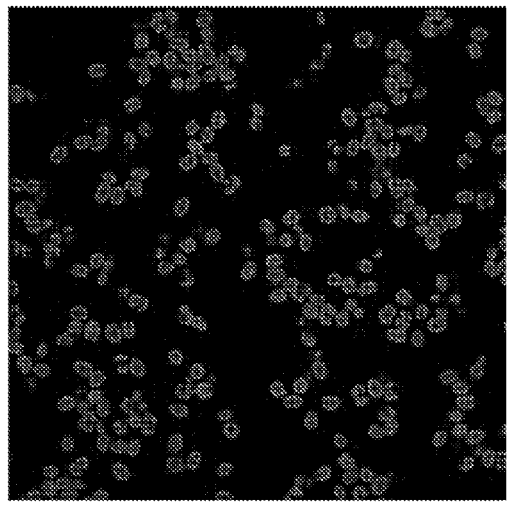
Figure 11G:
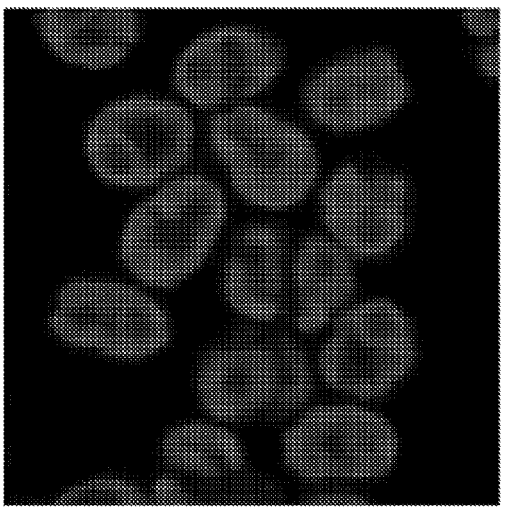
Figure 11H:
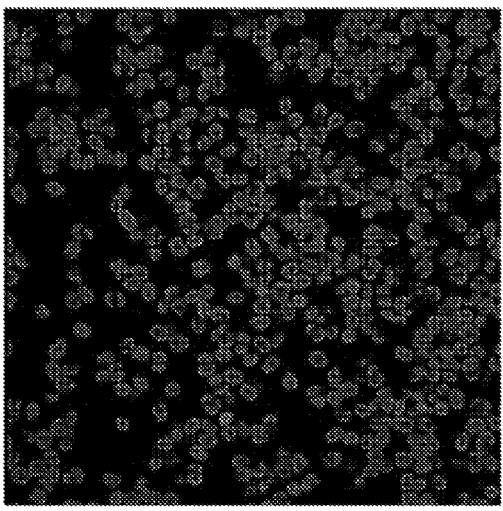

Thus, *C. reinhardtii* mutant cc-4350 was treated with Fl–4, Fl–8, and Fl–10 at concentrations of 12.5, 25 and 50 µM. Fluorescein alone (Fl) and non-covalent 1:1 mixtures of fluorescein and r8 (Fl+r8) at the same concentrations were used as controls. The cells were then analyzed by flow cytometry to determine levels of fluorescence. As had been observed in mammalian systems, both Fl itself and the non-covalent mixture of Fl and r8 (Fl+r8) did not show any uptake. In striking contrast, the Fl–8 covalent conjugate showed robust concentration-dependent uptake, behaving much as it does in the previously studied mammalian systems (Wender et al. (2000) *Proc. Natl. Acad. Sci. USA* 97: 13003-13008) (FIG. 1A, Fl-4 and Fl-10 data can be seen in FIG. 7). To determine whether the fluorescent compounds had been internalized or simply deposited on the cell surface, high-resolution confocal Z-stack fluorescent images were taken of cell wall-deficient cc-4350 cells after treatment with either the non-covalent Fl+r8 control or the Fl-8 conjugate (FIGS. 1B and 1C). The Z-stack images indicated that Fl-8 was indeed internalized, whereas in setting-matched images of cells treated with Fl+r8 controls there was no apparent internalization.

Figure 1F:
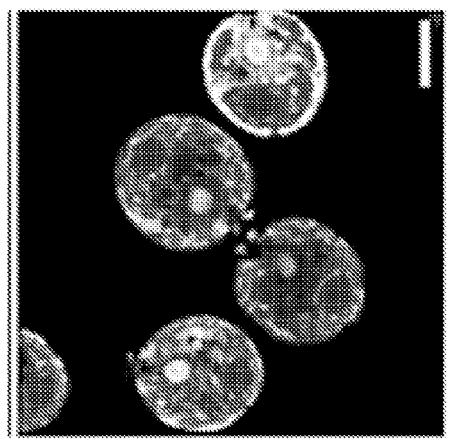
Figure 1D:
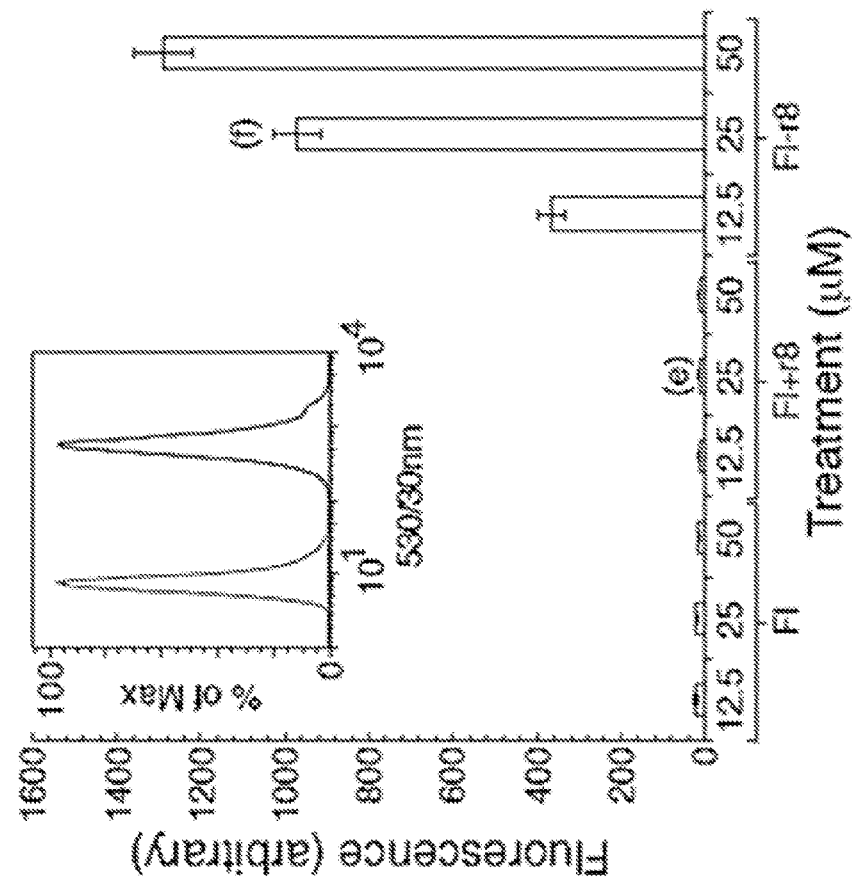
Figure 2A:
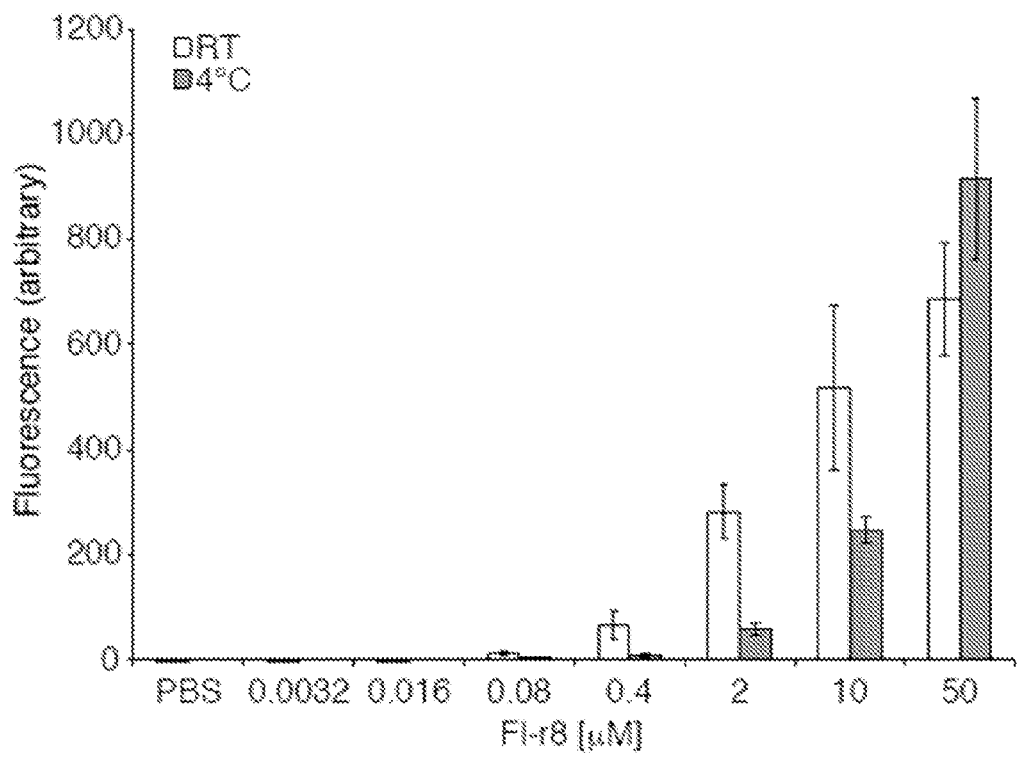
FIGS. 2A-2D shows a series of graphs illustrating the results of flow cytometry data of *C. reinhardtii* treated at 4° C., in the dark, and after acid-induced deflagellation. In all graphs the mean fluorescence is plotted, error is SD.
Figure 2B:
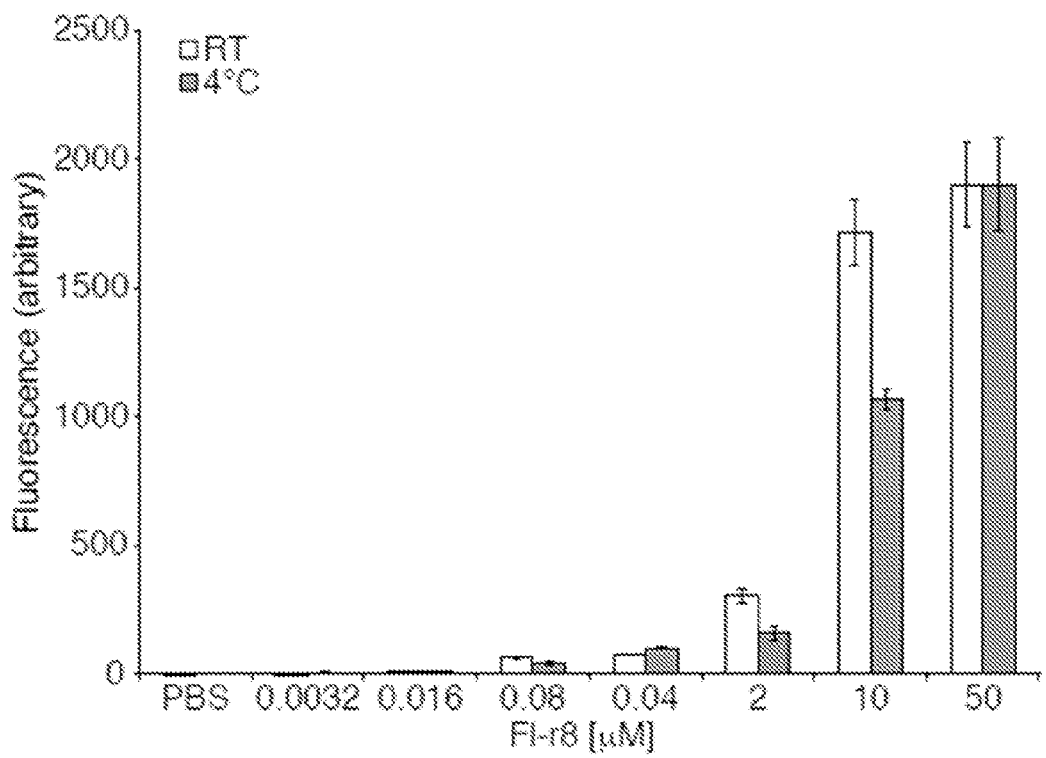
Figure 2C:
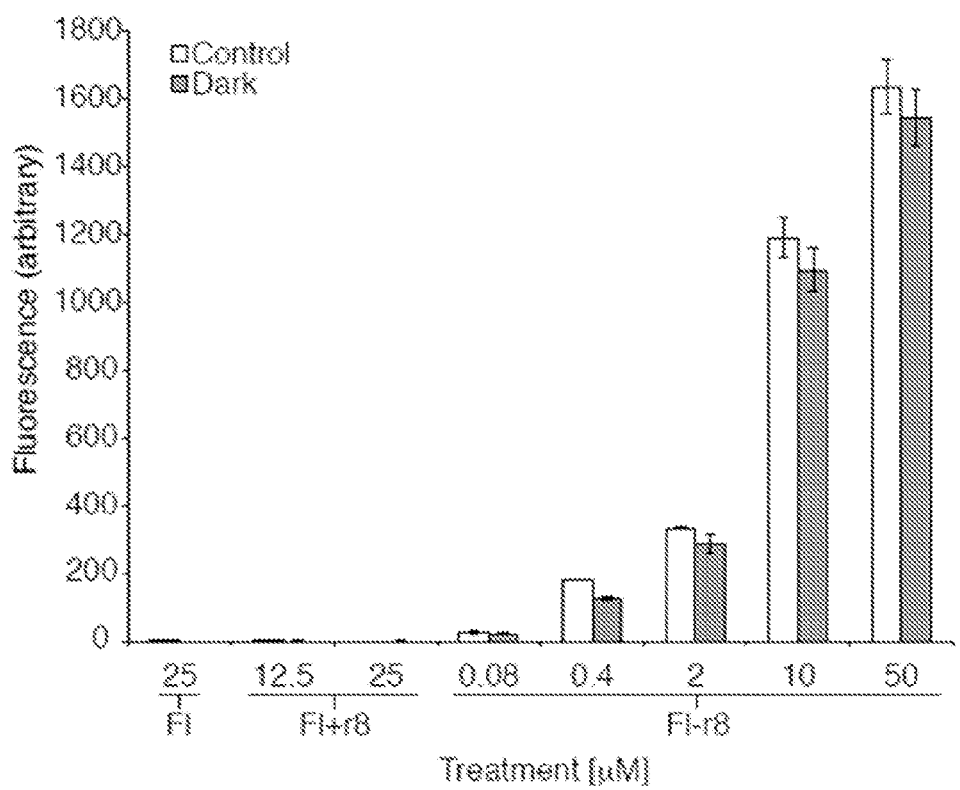
Figure 2D:
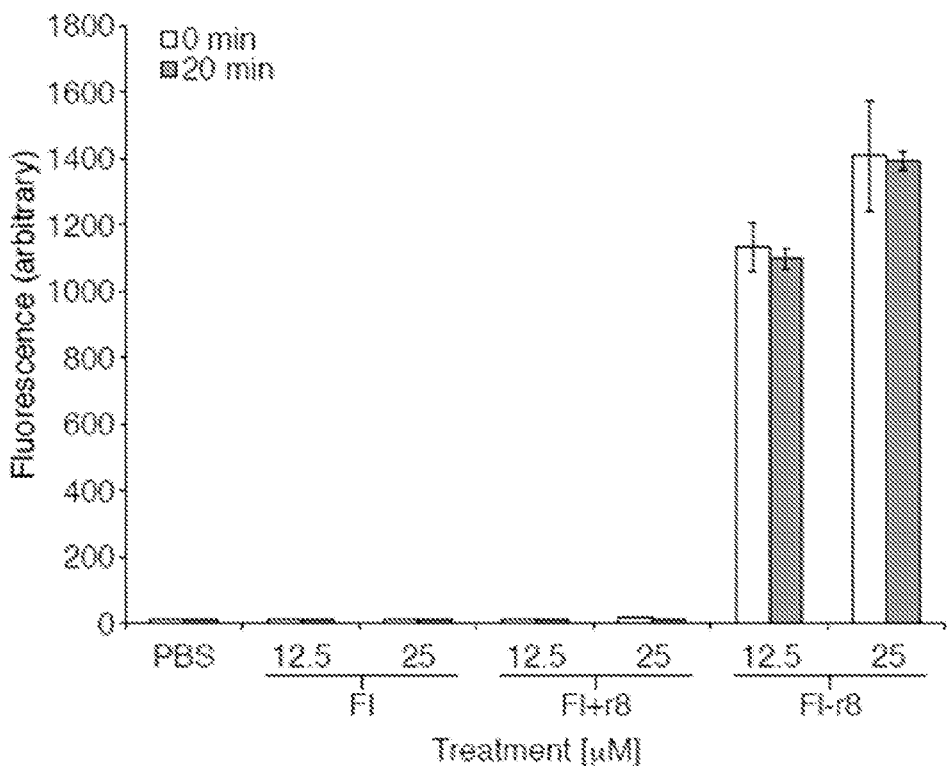

To determine next whether these GR-MoTrs are capable of penetrating the cell wall, wild-type *C. reinhardtii* were treated with the Fl-oligoarginine conjugates. Uptake of the conjugates was analyzed by flow cytometry (FIG. 1D, Fl-4). Fl-10 can be seen in FIG. 7. Significantly, the wild-type algae showed robust uptake of the Fl-8 conjugate, but no uptake of Fl itself or of the non-covalent mixture of Fl+r8. The corresponding confocal Z-stack images of the treated cells revealed that Fl-8 had been internalized, indicating that GR-MoTrs can cross both the cell wall and the cell membrane of *C. reinhardtii* (FIGS. 1E and 1F).

Having established that GR-MoTrs can enter wild-type cells, whether biochemical or physical changes affect delivery was investigated. Because *C. reinhardtii* behavior and cellular biochemistry are affected by the presence, direction, and intensity of light (Kreimer G (2009) *Curr. Genet.* 55: 19-43), treatment of wild-type *C. reinhardtii* with Fl-8 in the dark was examined and found not to affect uptake relative to a light-on control, as shown in FIG. 2. When *C. reinhardtii* cells were pre-incubated and treated at 4° C. (a condition that slows or shuts down endosomal uptake pathways as well as many enzymatic functions) there was a weak, dose-dependent effect on Fl-8 uptake (FIG. 2), which differs from the more dramatic reduction in uptake seen in mammalian cells (Wender et al. (2000) *Proc. Natl. Acad. Sci. USA* 97: 13003-13008).

Wild-type *C. reinhardtii* have two flagella enclosed in a membrane but not a cell wall. To determine if uptake into the wild-type cells was occurring primarily or solely through the flagella, deflagellated *C. reinhardtii* were prepared using acid shock (Hartzell et al., (1993) *Exp. Cell Res.* 208: 148-153) and tested for uptake of the Fl-8 covalent conjugate in a time-dependent manner. There was no apparent decrease in the amount of uptake, or in the percentage of cells taking in Fl-8 in the deflagellated cells, as shown in FIG. 2.

Delivery to Other Species of Algae: Although *C. reinhardtii* is arguably the most studied and commonly used model algae in academic research, there are many species of algae that are of academic as well as industrial interest for which few molecular tools exist. In addition, it is well known that different species of algae have widely varying cell wall compositions (Abo-Shady et al., (1993) *Biologia Plantarum* 35: 629-632), and as such provide a unique opportunity to investigate how barrier type affects GR-MoTr entry.

Accordingly, several green algae species in the class Chlorophyceae, including *Neochloris oleoabundans, Scenedesmus dimorphus, Chlorella protothecoides* and *Botryococcus braunii* were tested. Dramatic species-specific differences in uptake of Fl-8 were observed. Fluorescent images of the species revealed that some internalize Fl-8 similarly to *C. reinhardtii* (*N. oleoabundans*) and others become coated with Fl-8 (*C. protothecoides*) (as shown in FIGS. 3A-3H). Still other species, such as *S. dimorphus* and *B. braunii*, display complex behavior within a single population of cells, with some cells showing internalization of Fl-8, some showing cell surface staining with Fl-8, and some remaining unstained. These differences might be explained by the morphological heterogeneity of *S. dimorphus* (Cepák et al., (2006) *Folia Microbiol.* 51: 349-356), and by the complex extracellular matrix of *B. braunii* (Casadevalli et al., (1985) *Biotechnol. Bioeng.* 27: 286-295).

Figure 3I:
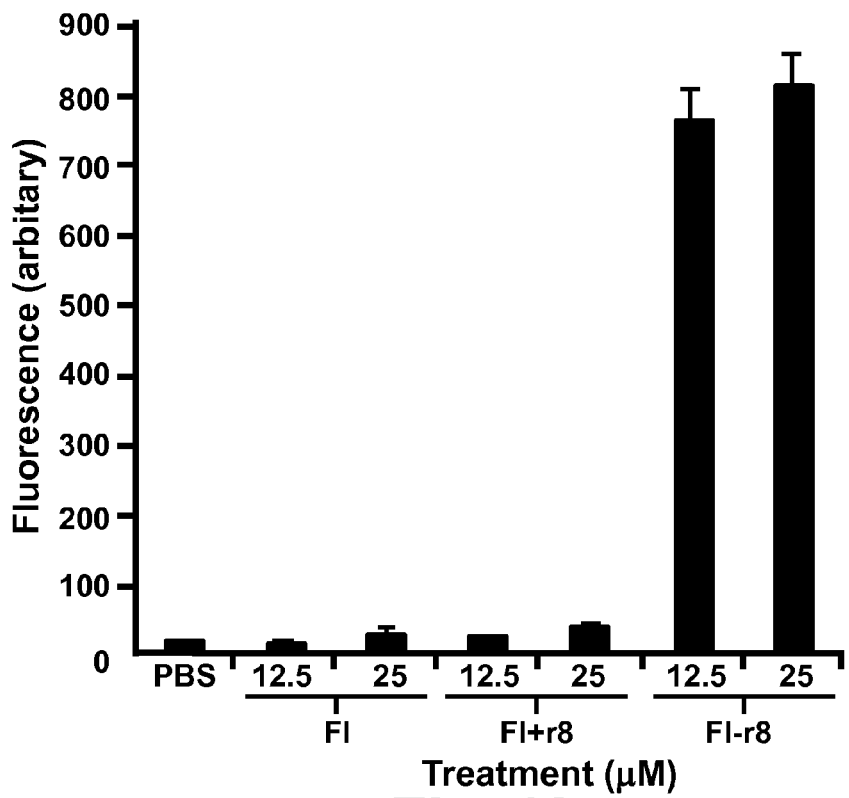
FIGS. 3I-3K is a series of graphs illustrating the mean fluorescence as determined by flow cytometry of *S. dimorphus* (FIG. 3I), *C. protothecoides* (FIG. 3J), and *N. oleoabundans* (FIG. 3K) treated with conjugates and controls.
Figure 3J:
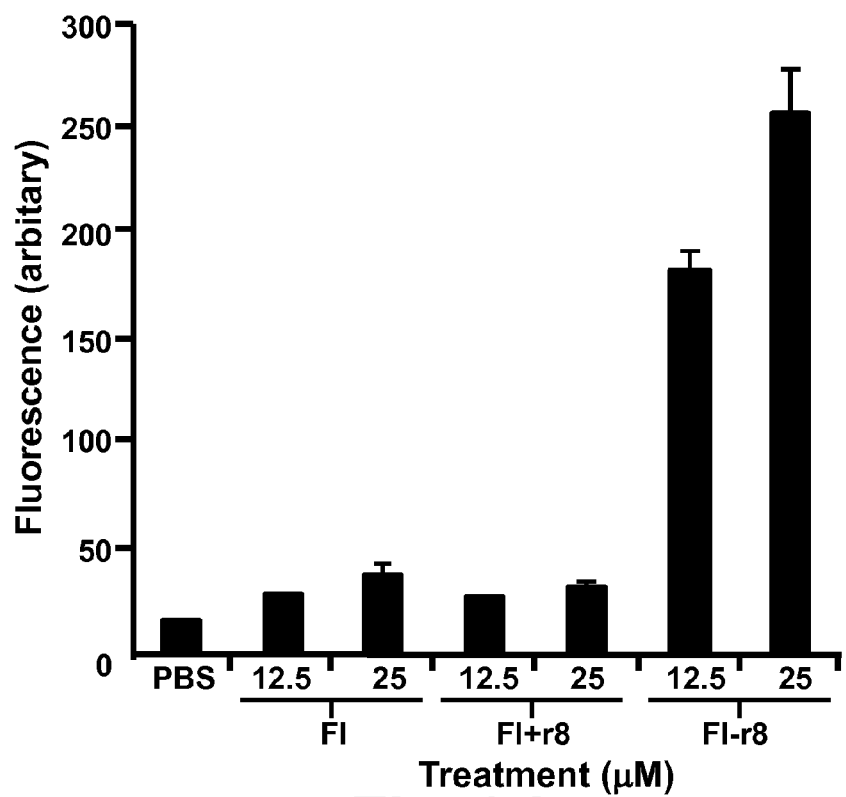
Figure 3K:
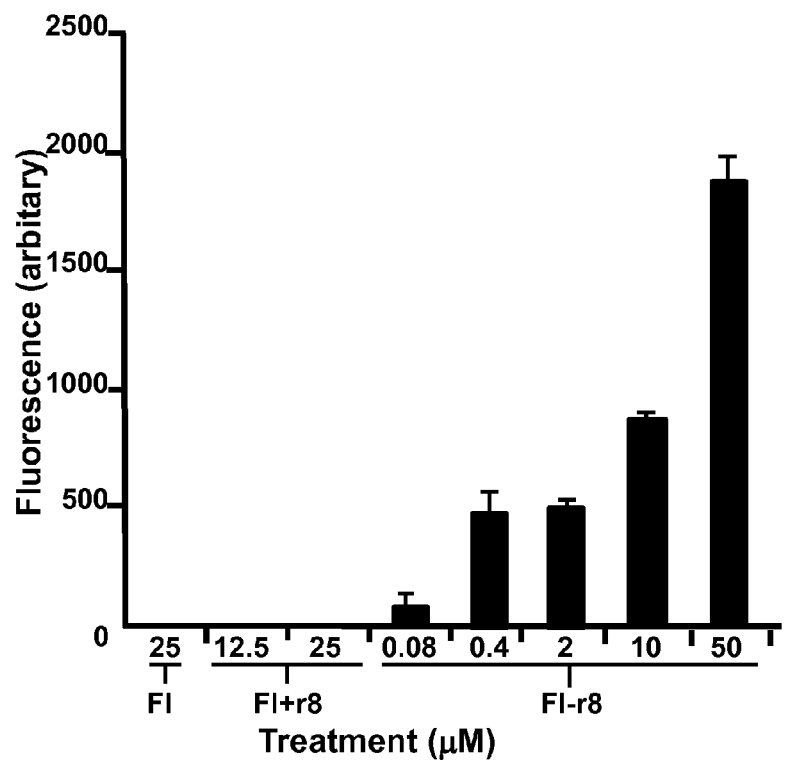
Figure 4A:
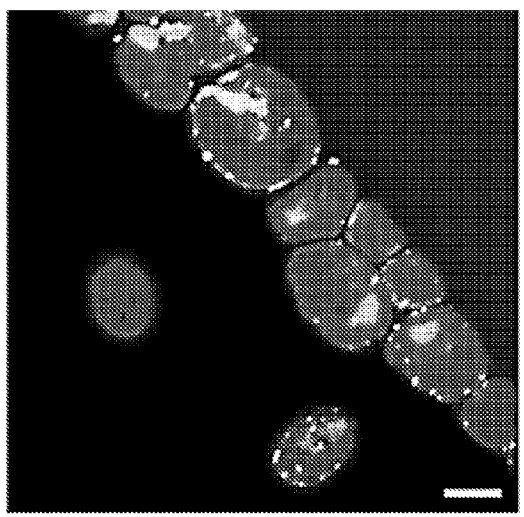
FIGS. 4A-4D illustrate the results of fluorescence microscopy and flow cytometry of wild-type *C. reinhardtii* treated with either FAM-streptavidin, FAM-streptavidin and nona-arginine (with no biotin), or FAM-streptavidin-biotin-R9 complex.
Figure 4B:
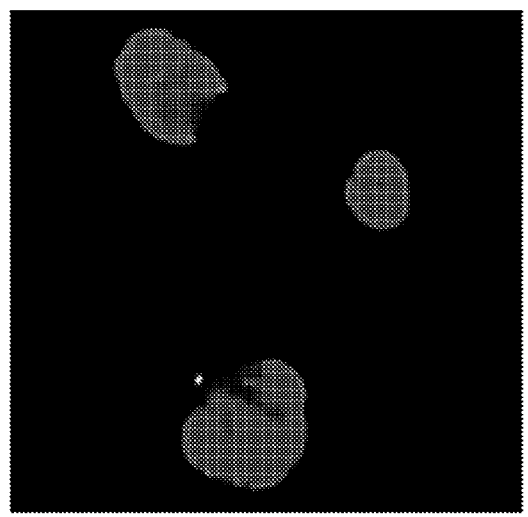
Figure 4C:
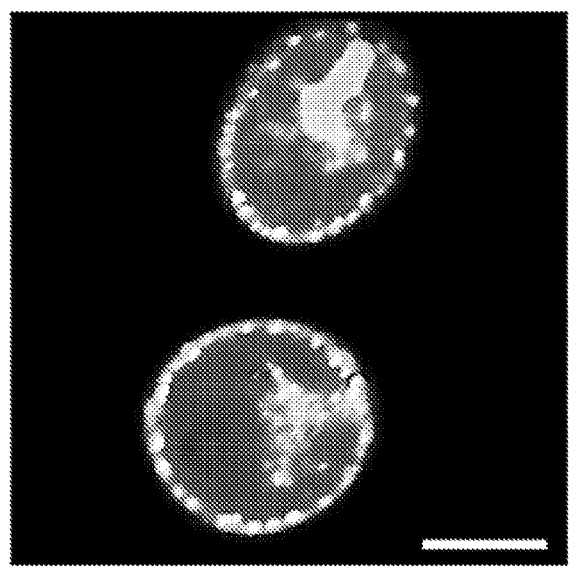
Figure 4D:
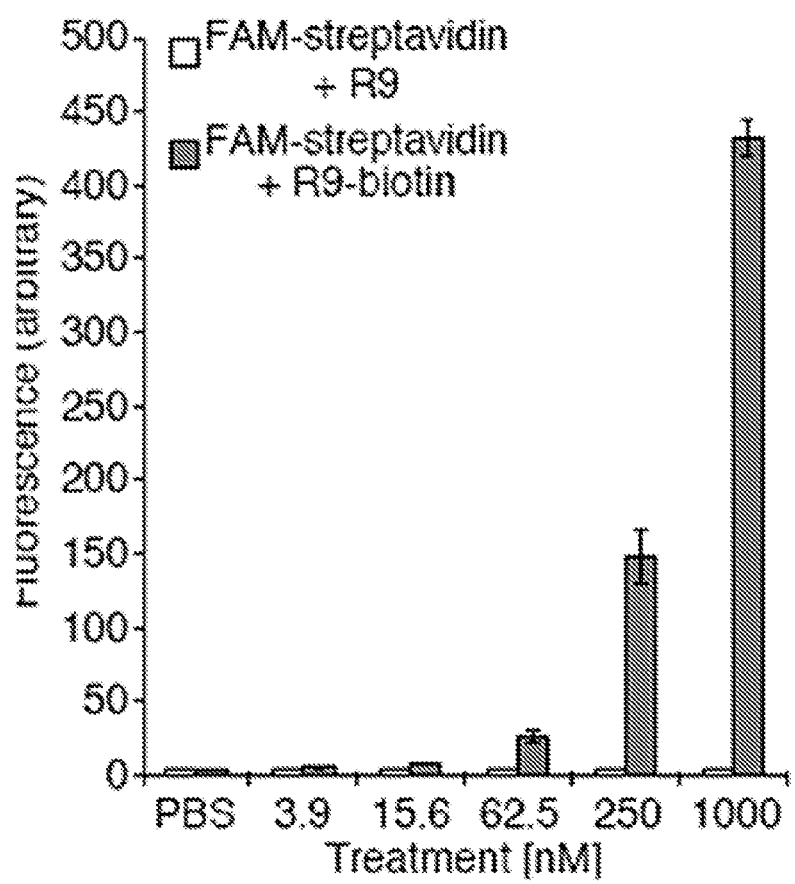

Flow cytometry was performed with those species that showed either internalization or cell surface staining to determine if the uptake pattern was similar to that of *C. reinhardtii* as shown in FIGS. 3I-3K). The species-specific differences in uptake of the GR-MoTrs could be utilized for algal cell differentiation in mixtures of species by either fluorescence microscopy or flow cytometry (as shown in FIG. 8). These species-specific differences also present opportunities for the selective manipulation of species.

Delivery of Protein Cargo: The efficient delivery of small molecules and probes, such as fluorescein, into algal cells creates new avenues by which algae can be imaged and manipulated. For other applications, however, delivery of larger cargos (e.g. biomacromolecules, quantum dots, nanoparticles) is required. To address this significant challenge, a biotin-labeled arginine 9-mer (biotin-R9) non-covalently complexed to FAM-labeled streptavidin (FAM-streptavidin) was incubated with wild-type *C. reinhardtii*. As controls, cells were treated with either FAM-streptavidin alone, or a mixture of FAM-streptavidin and nona-arginine (i.e. nona-arginine with no biotin conjugation) at the same concentrations used with the FAM-streptavidin-biotin-R9. No uptake was observed with either of the controls. In contrast, effective uptake was observed with the approximately 60 kDa GR-MoTr-protein complex (as shown in FIGS. 4 and 9).

Biological barriers are critical to cellular life but at the same time severely limit, due to size, log P, charge, and other physical properties, the universe of tools and methods that can be used for the study and manipulation of cells. This limitation is exacerbated in organisms like algae that have both a cell wall and membrane barrier yet represent a potentially bountiful source of molecules for research, industrial and clinical applications. Using the model organism *C. reinhardtii* as well as other algal species, the present disclosure encompasses embodiments of a general molecular method for delivering both small and large cargo into algae. This represents a novel example of a GR-MoTr-mediated means of transport into a broad range of species of algae, and notably involves efficient passage across both cell wall and membrane barriers. This method was shown to work with a protein cargo using *C. reinhardtii* as a representational species The methods of the disclosure provide opportunities in algal research that required an efficient and effective means of delivering molecules such as drugs, metabolic intermediaries, labeling compounds and the like to the cells and which had previously been limited to cell wall-free systems. The methods of the disclosure are also suitable for the delivery to algal cells, including those cells having an intact cell wall including, but not limited to, the delivery of small molecule probes (Stewart et al., (2008) *Org. Biomol. Chem.* 6: 2242-2255), peptides and proteins (Stewart et al., (2008) *Org. Biomol. Chem.* 6: 2242-2255; Deshayes et al., (2010) *Biochim. Biophys. Acta* 1798: 2304-2314; Schwarze et al., (1999) *Science* 285: 1569-1572; Zhou et al., (2009) *Cell Stem Cell* 4: 381-384), genetic material (Stewart et al., (2008) *Org. Biomol. Chem.* 6: 2242-2255; Deshayes et al., (2010) *Biochim. Biophys. Acta* 1798: 2304-

2314; Won et al., (2010) et al., *Mol. Ther.* 18: 734-742; Lehto et al. (2010) *J. Control. Rel.* 141: 42-51; Siprashvili et al. (2003) *Hum. Gene Ther.* 14: 1225-1233, 34-36), and radioactive tracers (Constantini et al., (2008) *Cancer Biotherapy and Radiopharmaceuticals* 23: 3-24). Species-specific and selective targeting with additional vectors and control of intracellular cargo release are also possible (Jones et al. (2006) *J. Am. Chem. Soc.* 128: 6526-6527). Given the breadth of our findings, GR-MoTrs could prove useful with many other industrially significant or academically interesting species for which there are currently no established molecular manipulation or transformation techniques.

One aspect of the present disclosure, therefore, encompasses embodiments of a method of delivering a cargo compound to an algal cell, comprising contacting an algal cell with a composition comprising a guanidinium-rich delivery vehicle comprising a guanidinium-rich molecular transporter (GR-MoTr) linked to a cargo compound desired to be delivered to the algal cell, whereby the guanidinium-rich molecular transporter can traverse the algal cell wall, thereby delivering the cargo compound to the algal cell.

In embodiments of this aspect of the disclosure, the guanidinium-rich molecular transporter can be a guanidinium-rich cell-penetrating peptide comprising from about 6 to about 25 guanidinium side-chains where at least three of the guanidinium side-chains are contiguous.

In embodiments of this aspect of the disclosure, the guanidinium-rich delivery vehicle can further comprise a linker moiety disposed between the guanidinium-rich molecular transporter (GR-MoTr) and the cargo compound.

In embodiments of this aspect of the disclosure, the linker can be cleavable.

In embodiments of this aspect of the disclosure, the cargo compound can be a small molecule, a nucleic acid, or a peptide.

In embodiments of this aspect of the disclosure, the small molecule can be a reporter molecule, an imaging contrast agent, an enzyme agonist, an enzyme antagonist, and a gene expression modulator.

In embodiments of this aspect of the disclosure, the algal cell is a member of an algal group selected from the group consisting of: Chlorophyceae Bacillariophyceae, Eustigmatophyceae, and Chrysophyceae.

In embodiments of this aspect of the disclosure, the algal cell is a *Chlamydomonas* species, a *Botryococcus* species, a *Chlorella* species, a *Neochloris* species, and a *Scenedesmus* species.

In embodiments of this aspect of the disclosure, the algal cell is *Chlamydomonas reinhardtii, Botryococcus braunii, Chlorella protothecoides, Neochloris oleoabundans*, or *Scenedesmus dimorphus*.

Another aspect of the disclosure encompasses embodiments of a method of isolating a sub-population of algal cells from a mixture of algal species, comprising: (a) contacting a population of algal cells with a composition comprising a guanidinium-rich delivery vehicle comprising a guanidinium-rich molecular transporter (GR-MoTr) linked to a label moiety, whereby the guanidinium-rich molecular transporter traverses the cell walls of a sub-population of algal cells, thereby delivering the label moiety to the cells of the sub-population of algal cells; (b) detecting the label moiety in the sub-population of algal cells; and (c) isolating the sub-population of algal cells, wherein said sub-population is characterized as having the capacity to receive a guanidinium-rich delivery vehicle across the cell walls thereof.

In embodiments of this aspect of the disclosure, the population of algal cells is a heterogeneous population of algal species.

In embodiments of this aspect of the disclosure, the label moiety is a fluorescent label and the sub-population of algal cells is isolated by FACS.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

EXAMPLES

Example 1

Materials: All *Chlamydomonas* strains were from the *Chlamydomonas* center, other species of algae were purchased from the culture collection at the University of Texas at Austin (UTEX). Fluorescein sodium salt was purchased from Sigma-Aldrich (St. Louis, Mo.) and used as purchased. Octa-(D)-arginine was obtained from UCB bioproducts. Fluorescein-oligo-(D)-arginine conjugates were synthesized via a peptide synthesizer as previously reported (12). Nona-(L)-arginine-biotin conjugate (#64708) and FAM-Streptavidin (#60664) were obtained from Anaspec (Fremont, Calif. 94555).

Example 2

Growth and maintenance of strains: *Chlamydomonas reinhardtii* strains were grown in Tris-acetate-phosphate (TAP) medium or TAP medium supplemented with 2 mM arginine (as necessary) under a 16:8 light:dark cycle. Cells were grown in 50 ml or 100 ml suspension culture in Erlenmeyer flasks and used generally at a concentration of $3 \times 10^6$ cells/ml. Wild-type strain cc-124 was used as was cell wall mutant cc-4350.

Other species were grown generally in the same manner, with variations in media as appropriate: *Botryococcus braunii* was grown in Waris+soil extract; *Chlorella protothecoides* in TAP media; *Neochloris oleoabundans* in TAP+Arg; and *Scenedesmus dimorphus* in TAP media. All cell lines were kept on both solid and in liquid culture, and new liquid cultures were started periodically off of plates.

Example 3

Flow Cytometry Experiments: 6×10$^5$ cells/well were plated in conical-bottomed 96-well plates, supernatant was removed and 200 µl of treatment (12.5 µM, 25 µM, or 50 µM of fluorescein alone Fl), noncovalent fluorescein, fluorescein and r8 (Fl–8), Fl–4, Fl–8, or Fl–r10) was applied for 5 min. All conditions were in triplicate. Cells were spun at 1,500 rpm for 5 min in an eppendorf 3810 centrifuge equipped with a plate rotor, supernatant was removed and replaced with 200 µl PBS. Plates were spun again, wash was removed and replaced with 200 µl PBS, and wells were analyzed using a FACscaliber (BD Biosciences) equipped with a 96-well sampler attachment running Platemanager and Cellquest. All analysis was performed using FlowJo (Tree Star software).

Experiments for testing the effect of cold temperatures on cellular uptake were performed with the same conditions except as follows: cells were cooled to 4° C. for 5 min previous to start, treatments and washes were precooled to 4° C. All procedures were carried out on ice, and centrifugation was performed at 4° C.

Experiments testing the effects of a transfer to dark conditions on uptake were performed in a darkroom for all steps, followed by covering plates with aluminum foil for centrifugation.

Experiments using mixtures of algal species were performed as above, but mixtures were plated such that their total cell count was 6×10$^5$ cells/well. Mixtures shown were a 1:1:1 ratio containing equal numbers of *C. reinhardtii* cc-124, *S. dimorphus*, and *N. oleoabundans*.

Example 4

Deflagellation: Cells at 3×10$^6$ cells/ml were acidified to pH 4.5 with 0.5 M acetic acid for 60 s, then brought rapidly back to about pH 7.2. Cells were immediately centrifuged and then treated, or left without shaking and samples taken at 0 and 20 min.

Example 5

FAM-streptavidin uptake experiments: Protein delivery experiments were performed using a nona-(L)-arginine-biotin conjugate and a FAM-streptavidin conjugate (Anaspec, Fremont, Calif.). Reagents were prepared according to the manufacturer. Reagents were mixed at a 4:1 (R9-biotin:FAM-streptavidin) ratio in PBS. Final concentrations for FAM-Streptavidin and R9-biotin were 200 nM and 800 nM respectively. The mixture was allowed to sit for 30 min. Wild type *C. reinhardtii* (6×10$^5$) cells were pelleted at 1500 rpm for 5 min then mixed with the R9-biotin-FAM-streptavidin mixture or FAM-streptavidin alone and allowed to sit for 30 min. Cells were then pelleted at 1500 rpm for 5 min and washed with 200 µl PBS. Cells were pelleted again, supernatant was removed, and 5 µl PBS was added before placing on slides, or 200 µl PBS was added for FACS experiments.

Example 6

Microscopy Experiments: All microscopy was performed with a Zeiss LSM710 confocal microscope using 488 nm and 663 nm laser lines. Images for Fl–8 and controls were taken with matched settings for each pair of images (x-y-z resolution, bit-depth, averaging, pixel dwell-time, digital zoom, laser energy, pinhole and exposure). Cells were prepared as for FACS experiments, however after the final wash cells were brought up in 5 µl PBS. Slides were prepared with a thin layer of 1% agarose, and cells were placed on the agarose then covered with a cover slip. Care was taken to ensure that cells were disturbed as little as possible, and small holes were made in the agarose to allow some bubbles of liquid to form on each slide, allowing comparison between samples that were free swimming and samples that were pinned between agarose and the cover slip. Samples prepared in this manner and not disrupted were found to be viable for several days.

Example 7

Synthesis of covalently Linked fluorescein-oligo-(D)-arginine conjugates of 4, 8, and 10 arginines (Fl–4, Fl–8, Fl–10, respectively): The conjugates were synthesized as described in Wender et al., (2000) *Proc. Natl. Acad. Sci. U.S.A.* 97: 13003-13008, incorporated herein by reference in its entirety. Briefly, homopolymers of arginine were prepared with an automated peptide synthesizer (ABI433) by using standard solid-phase fluorenylmethoxycarbonyl (Fmoc) chemistry with HATU as the peptide coupling reagent. The fluorescein moiety (Fl) was attached via an aminohexanoic acid spacer by treating a resin-bound peptide (1.0 mmol) with FITC (1.0 mmol) and diisopropyl ethyl amine (5 mmol) in dimethylformamide (DMF; 10 ml) for 12 h. Cleavage from the resin was achieved by using 95:5 trifluoroacetic acid (TFA)/triisopropylsilane. Removal of the solvent in vacuo gave a crude oil that was triturated with cold ether. The crude mixture thus obtained was centrifuged, the ether was removed by decantation, and the resulting orange solid was purified by RP-HPLC ($H_2O/CH_3CN$ in 0.1% TFA). The products were isolated by lyophilization and characterized by electrospray mass spectrometry. The purity of the peptides was >95% as determined by analytical RP-HPLC ($H_2O/CH_3CN$ in 0.1% TFA).

Example 7

HPR-Streptavidin Uptake Experiments: Protein delivery experiments were performed using a nona-(L)-arginine-biotin conjugate (Anaspec, Fremont, Calif.) and a horseradish peroxidase-streptavidin conjugate (HRP-streptavidin) (Life Sciences, Grand Island, N.Y.). Control experiments also utilized nona-arginine (R9, i.e., not conjugated to biotin). Reagents were prepared according to the manufacturer. Reagents were mixed at a 4:1 (biotin-R9 to HRP-streptavidin) ratio in PBS. Final concentrations for HRP-streptavidin and biotin-R9 were 1 µM and 4 µM, respectively. The mixture was allowed to sit for 10 min. For the control, reagents were mixed at a 4:1 (R9 to HRP-streptavidin) ratio in PBS. Final concentrations were the same as above and the mixture was allowed to sit for 10 min. Wild-type *C. reinhardtii* or mutant cc-4350 cells (2×10$^6$) were pelleted at 1,500 rpm for 5 min then mixed with the HRP-streptavidin: biotin-R9 complex, R9 and HRP-streptavidin mixture, HRP-streptavidin alone, or biotin-R9 alone and allowed to sit for 20 min. Cells were then pelleted at 1,500 rpm for 5 min and washed with 400 µL PBS. Cells were pelleted again, the supernatant was removed, and 80 µL PBS was added. Forty microliters of this cell solution was added to two different wells in a labtek eight-well multiwell coverslip. Multiwell coverslips were prepared by adding 200 µL of 0.1 µg/mL concanavalin A per well, incubating for 20 min, removing the liquid, and allowing it to dry completely. Once cells had adhered to the multiwell coverslips, 360 µL of 4% paraformaldehyde (PFA) was added, and cells were fixed for 15 min. PFA was removed and 300 mL of ECL reagent (Supersignal West Femto, Pierce Biotechnology, Rockford Ill.) or PBS was added to each well. After 30 min, supernatant was removed from each well, and 100 µL Prolong Gold mounting media (Life Sciences, Grand Island, N.Y.) was added to each well and images were taken using a Zeiss LSM710 as for other experiments. All images were taken with the same settings for direct comparison.

We claim:

1. A method of delivering a cargo compound to an algal cell, the method comprising contacting an algal cell with a guanidinium-rich delivery vehicle comprising a guanidinium-rich molecular transporter (GR-MoTr) linked to a cargo compound desired to be delivered to the algal cell; and allowing the guanidinium-rich molecular transporter to traverse the algal cell wall, thereby delivering the cargo compound to the algal cell.

2. The method of claim 1, wherein the guanidinium-rich molecular transporter is a guanidinium-rich cell-penetrating peptide comprising from about 6 to about 25 guanidinium side-chains and wherein at least three of the guanidinium side-chains are contiguous.

3. The method of claim 1, wherein the guanidinium-rich delivery vehicle further comprises a linker moiety disposed between the guanidinium-rich molecular transporter (GR-MoTr) and the cargo compound.

4. The method of claim 3, wherein the linker is cleavable.

5. The method of claim 1, wherein the cargo compound is a small molecule, a nucleic acid, or a peptide.

6. The method of claim 5, wherein the small molecule is selected from the group consisting of a reporter molecule, an imaging contrast agent, an enzyme agonist, an enzyme antagonist, and a gene expression modulator.

7. The method of claim 1, wherein the algal cell is a member of an algal group selected from the group consisting of: *Chlorophyceae*, *Bacillariophyceae*, *Eustigmatophyceae*, and *Chrysophyceae*.

8. The method of claim 1, wherein the algal cell is selected from the group consisting of a *Chlamydomonas* species, a *Botryococcus* species, a *Chlorella* species, a *Neochloris* species, and a *Scenedesmus* species.

9. The method of claim 8, wherein the algal cell is *Chlamydomonas reinhardtii*, *Botryococcus braunfi*, *Chlorefia protothecoides*, *Neochloris oleoabundans*, or *Scenedesmus dimorphus*.

10. A method of isolating a sub-population of algal cells, comprising:
(a) contacting a population of algal cells consisting of a plurality of sub-populations, with a composition comprising a guanidinium-rich delivery vehicle comprising a guanidinium-rich molecular transporter (GR-MoTr) linked to a label moiety, whereby the guanidinium-rich molecular transporter traverses the cell walls of a recipient sub-population of algal cells but not the cell walls of other sub-populations, thereby delivering the label moiety to the cytoplasm of the cells of the recipient sub-population of algal cells;
(b) detecting the label moiety in the said recipient sub-population of algal cells; and
(c) isolating the sub-population of algal cells, wherein said sub-population is characterized as having the capacity to receive a guanidinium-rich delivery vehicle across the cell walls thereof.

11. The method of claim 10, wherein the label moiety is a fluorescent label and the sub-population of algal cells is isolated by fluorescence activated cell sorting (FACS).

12. The method of claim 10, wherein the population of algal cells consists of a single algal species, and wherein the subpopulations thereof are distinguishable by a capacity to receive a guanidinium-rich delivery vehicle across the cell walls thereof.

13. The method of claim 10, wherein the population of algal cells consists of a plurality of algal species, wherein at least one of the algal species comprises of a sub-population having the capacity to receive a guanidinium-rich delivery vehicle across the cell walls thereof.

* * * * *